(12) United States Patent
Ward et al.

(10) Patent No.: US 10,314,532 B2
(45) Date of Patent: Jun. 11, 2019

(54) EVALUATING CARDIOVASCULAR HEALTH USING INTRAVASCULAR VOLUME

(71) Applicant: THE REGENTS OF THE UNIVERSITY OF MICHIGAN, Ann Arbor, MI (US)

(72) Inventors: Kevin Ward, Superior Township, MI (US); Mohamad Hakam Tiba, Ann Arbor, MI (US); James M. Blum, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1327 days.

(21) Appl. No.: 14/445,926

(22) Filed: Jul. 29, 2014

(65) Prior Publication Data

US 2015/0031966 A1    Jan. 29, 2015

Related U.S. Application Data

(60) Provisional application No. 61/859,615, filed on Jul. 29, 2013.

(51) Int. Cl.
*A61B 5/0205*    (2006.01)
*A61B 5/0295*    (2006.01)
(Continued)

(52) U.S. Cl.
CPC .......... *A61B 5/4836* (2013.01); *A61B 5/0205* (2013.01); *A61B 5/0535* (2013.01);
(Continued)

(58) Field of Classification Search
CPC ... A61B 5/4836; A61B 5/0205; A61B 5/0535; A61B 5/4884; A61B 5/7278; A61B 5/0075; A61B 5/0261; A61B 5/0295; A61B 5/0533; A61B 5/0816; A61B 5/1073; A61B 5/1075; A61B 5/14551; A61B 5/6822; A61B 5/6824; A61B 5/7275; A61B 8/06
(Continued)

(56) References Cited

U.S. PATENT DOCUMENTS 3,730,171 A    5/1973   Namon
3,835,840 A    9/1974   Mount
(Continued)

FOREIGN PATENT DOCUMENTS

GB        1359531 A    7/1974

OTHER PUBLICATIONS

International Preliminary Report on Patentability from PCT/US2014/048641 dated Feb. 11, 2016.
(Continued)

*Primary Examiner* — Navin Natnithithadha
(74) *Attorney, Agent, or Firm* — Marshall, Gerstein & Borun LLP

(57) ABSTRACT

Non-invasive monitoring of cardiovascular health is performed by monitoring changes in the volume of blood in the venous side of the vascular system. The blood volume changes are determined from measurements of bioimpedance of limbs or neck, in particular changes in bioimpedance in response to blood modulating events performed on the limbs or neck, where bioimpedance is measured and compared before and after such events.

28 Claims, 16 Drawing Sheets

(51) Int. Cl.
  *A61B 8/06* (2006.01)
  *A61B 5/00* (2006.01)
  *A61B 5/053* (2006.01)
  *A61B 5/026* (2006.01)
  *A61B 5/08* (2006.01)
  *A61B 5/107* (2006.01)
  *A61B 5/1455* (2006.01)

(52) U.S. Cl.
  CPC .......... *A61B 5/4884* (2013.01); *A61B 5/7278* (2013.01); *A61B 5/0075* (2013.01); *A61B 5/0261* (2013.01); *A61B 5/0295* (2013.01); *A61B 5/0533* (2013.01); *A61B 5/0816* (2013.01); *A61B 5/1073* (2013.01); *A61B 5/1075* (2013.01); *A61B 5/14551* (2013.01); *A61B 5/6822* (2013.01); *A61B 5/6824* (2013.01); *A61B 5/7275* (2013.01); *A61B 8/06* (2013.01)

(58) Field of Classification Search
  USPC .................................................. 600/504–507
  See application file for complete search history.

(56) References Cited

U.S. PATENT DOCUMENTS

| | | | |
|---|---|---|---|
| 6,095,987 | A | 8/2000 | Shmulewitz et al. |
| 6,648,828 | B2 | 11/2003 | Friedman et al. |
| 6,676,608 | B1 | 1/2004 | Keren |
| 8,251,912 | B2* | 8/2012 | Shelley ................ A61B 5/0059 600/484 |
| 8,388,545 | B2* | 3/2013 | Keren ................... A61B 5/0535 600/481 |
| 9,675,294 | B2* | 6/2017 | Levin ..................... A61B 5/0537 |
| 2003/0167012 | A1 | 9/2003 | Friedman et al. |
| 2004/0044290 | A1 | 3/2004 | Ward et al. |
| 2005/0080460 | A1 | 4/2005 | Wang et al. |
| 2006/0122540 | A1 | 6/2006 | Zhu et al. |
| 2008/0097230 | A1 | 4/2008 | Marks et al. |
| 2008/0190430 | A1 | 8/2008 | Melker et al. |
| 2009/0287102 | A1 | 11/2009 | Ward |
| 2010/0036455 | A1 | 2/2010 | Sanders et al. |
| 2010/0222696 | A1 | 9/2010 | Feldkamp et al. |
| 2011/0046505 | A1 | 2/2011 | Cornish et al. |
| 2011/0077474 | A1* | 3/2011 | Huiku ................ A61B 5/02416 600/301 |
| 2012/0016246 | A1 | 1/2012 | Sandgaard |
| 2012/0095355 | A1 | 4/2012 | Zdeblick |
| 2013/0172691 | A1 | 7/2013 | Tran |
| 2014/0249384 | A1* | 9/2014 | Levin .................... A61B 5/0537 600/301 |

OTHER PUBLICATIONS

Extended European Search Report from European Application No. 14831201.0 dated Jun. 19, 2017.
International search report and written opinion from PCT/US2014/048641 dated Nov. 11, 2014.
Funk et al., "Role of the Venous Return in Critical Illness and Shock: Part II—Shock and Mechanical Ventilation," Critical Care Medicine, 41(2)1-7 (2013).
Funk et al., "The Role of Venous Return in Critical Illness and Shock—Part 1: Physiology," Critical Care Medicine, 41(1):255-262 (2013).
García et al., "Clinical applicability of functional hemodynamic monitoring," Annals of Intensive Care 1:35, pp. 1-4 (2011).
Maas et al., "Cardiac Output Response to Norepinephrine in Postoperative Cardiac Surgery Patients: Interpretation with Venous Return and Cardiac Function Curves," Critical Care Medicine, 41(1):143-150 (2013).
Marik et al., "The Use of Bioreactance and Carotid Doppler to Determine Volume Responsiveness and Blood Flow Redistribution Following Passive Leg Raising in Hemodynamically Unstable Patients," Chest 143(2):364-370 (2013).

* cited by examiner

EVALUATING CARDIOVASCULAR HEALTH USING INTRAVASCULAR VOLUME

CROSS-REFERENCE TO RELATED APPLICATIONS

The present application claims the benefit of U.S. Provisional Application No. 61/859,615, entitled "Evaluating Cardiovascular Health Using Intravascular Volume," filed on Jul. 29, 2013, which is hereby incorporated by reference herein in its entirety.

FIELD OF INVENTION

The present disclosure generally relates to a system and a method for evaluating a patient's cardiovascular health and, more particularly, to a non-invasive method for determining a patient's intravascular volume status by measuring the change in peripheral venous volume in response to an event causing blood to return to the heart via the venous system.

BACKGROUND

For patients suffering from a variety of injuries or disease states such as cardiac arrest, burns, trauma, heart failure, sepsis, dehydration from any cause, renal failure, or dialysis, it is important to monitor the relationship between the volume of circulating blood and the patient's ability to circulate that volume of blood. Further, in many medical conditions, it is important to know if patients will hemodynamically respond in a favorable manner to providing intravenous fluids and/or if they are volume overloaded. This is especially important in complex states such as sepsis and cardiogenic shock.

However, determination of a patient's intravascular volume status in a noninvasive manner has been problematic. Methods of monitoring cardiac output are commonly used to assess the condition of patient's suffering from a variety of conditions. However, many of the methods that are non-invasive fail to quantify the volume of blood circulating within the patient relative to the patient's ability to circulate that volume. These parameters are important because ideally the physician could adjust the volume of circulating blood (for example via intravenous fluids) in order to achieve optimum cardiovascular circulation or output. Recently, impedance cardiography has been used to measure changes in cardiac output (and thus stroke volume) in response to temporary central fluid provision by raising of the lower extremities. This approach, however, is expensive, generally does not provide sufficient measurement sensitivity or accuracy, and may not be an option to some patients. In particular, impedance cardiography may necessitate that a patient's lower extremities be raised by a health care provider and many further necessitate repetitive raising if used as an endpoint measure. In many instances, raising of the legs will not be possible due to lower extremity injury, pelvic fracture or in situations where the patient may have limb amputation. In addition, passive leg lifting, as a provocative volume challenge maneuver may be ill suited since limb volume will greatly vary between individuals and even potentially within an individual if it is used repetitively when impedance cardiography is used as the end-point of the maneuver. Further, impedance cardiography has not been used to guide a reduction of intravascular volume. Thus, a passive extremity lift when used in conjunction with impedance cardiography as a hemodynamic endpoint cannot be used as a continuous measure to guide therapy.

Another approach, using ultrasound of the inferior and superior vena cava, has been used to look at the changes in these large venous vessels in response to spontaneous and mechanical ventilation with great accuracy. The collapsibility of these large vessels during respiration is indicative of volume status including right atrial pressure and whether or not the patient will increase their cardiac output in response to intravenous fluid administration. However, despite its utility such monitoring is prohibitively cumbersome and expensive and requires an experienced ultrasound operator. Furthermore, ultrasonic measurement of the inferior and superior vena cava cannot be performed continuously for a relatively long period of time. Other technologies like pulse pressure variation and stroke volume variation have been used to examine arterial changes produced by volume induced changes in cardiac output caused by respiration. However, measuring the volume variation of the arterial system has been problematic for various reasons (e.g., various pharmaceuticals may alter arterial vascular stiffness and volume largely independent of total intravascular volume). Additionally, it is unknown whether such a technique will work in patients with very stiff arterial systems from calcific and chronic hypertension conditions. Also such techniques may also require that the tidal volume of the patient be carefully controlled.

SUMMARY

The present application describes techniques to non-invasively monitor cardiovascular system health by monitoring changes in the volume of blood in the venous system of the arms, legs, or neck of patients by using one or more methods of determining tissue volume and/or volume changes of an extremity such as an arm, leg, or neck of the patient. The volume or volume changes may be determined using impedance plethysmography, near infrared spectroscopy, photoplethysmography, galvanic skin response, laser Doppler flowmetry, or ultrasound; although in the illustrated examples techniques using impedance measurements and changes in impedance are detailed.

In an example, a method for evaluating the cardiovascular condition of a patient, the method includes: (a) recording a first impedance of a limb or extremity of the patient at a first time in response to receiving a first impedance reading from a plurality of sensors on a limb or extremity or neck; (b) after the occurrence of an event modulating blood return to the heart via the venous system of the patient, recording a second impedance of the limb or extremity or neck at a second time in response to receiving a second impedance reading from a plurality of sensors on a limb or extremity or neck, wherein the first impedance and the second impedance each correspond to a volume of blood flowing within the limb or extremity or neck; and (c) determining a change in venous blood volume between the first time and the second time by comparing the first impedance and the second impedance to determine a change in volume of blood.

In accordance with another example, a testing apparatus for evaluating the cardiovascular condition of a patient, the testing apparatus includes: one or more electrodes; one or more processors; a computer-readable memory storing non-transient instructions that when executed by the one or more processors cause the testing apparatus to: (a) use the one or more electrodes to record a first impedance of a limb or extremity or neck of the patient at a first time in response to receiving a first impedance reading from a plurality of sensors on a limb or extremity or neck; (b) after the occurrence of an event modulating blood return to the heart via the venous system of the patient, use the one or more electrodes to record a second impedance of the limb or extremity or neck at a second time in response to receiving a second impedance reading from a plurality of sensors on a limb or extremity or neck, wherein the first impedance and the second impedance each correspond to a volume of blood flowing within the limb or extremity or neck; and (c) determine a change in venous blood volume between the first time and the second time by comparing the first impedance and the second impedance to determine a change in volume of blood.

In accordance with yet another example, a closed-loop cardiovascular condition evaluation system including: a testing apparatus; and a processor and a memory, the memory storing instructions that when executed by the processor, cause the processor to evaluate a cardiovascular condition of a subject in response to determining the change in the venous blood volume between the first time and the second time determined by comparing the first impedance and the second impedance, for different treatment cycles.

In accordance with yet another example, a method for evaluating the cardiovascular condition of a patient, the method includes: (a) determining a first volume of blood of a limb or extremity or neck of the patient at a first time; (b) after the occurrence of an event causing blood to return to the heart via the venous system of the patient, determining a second volume of blood of the limb or extremity or neck at a second time; (c) determining a change in venous blood volume between the first time and the second time by comparing the first volume of blood and the second volume of blood; and (d) determining one or more of: (1) how the patient will hemodynamically respond to one or more of an addition of cardiovascular fluid or removal of cardiovascular fluid, (2) how the patient will hemodynamically respond to one or more cardiovascular drugs which promote changes in cardiac output, changes in cardiovascular preload, and changes in cardiovascular afterload, or (3) determining how the patient will response to changes in mechanical or non-invasive ventilation.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Figure 1:
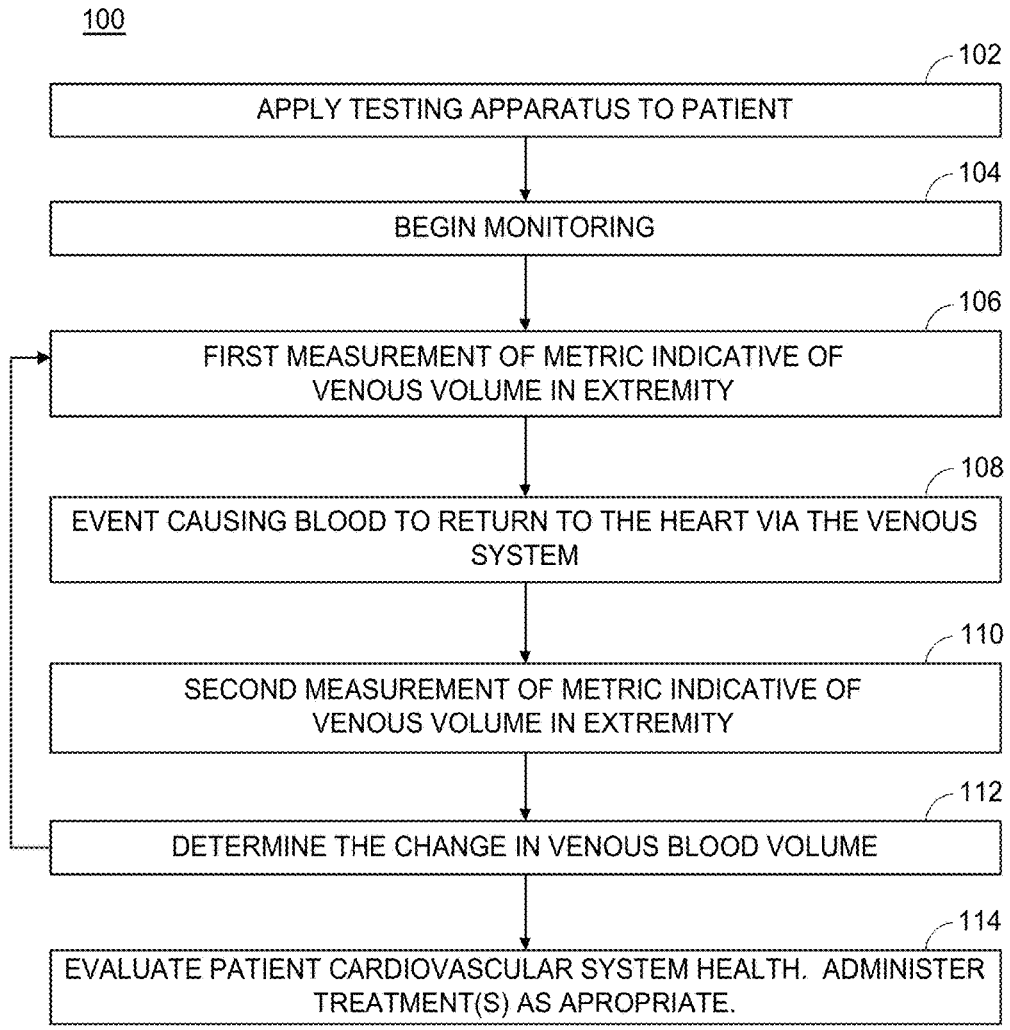
FIG. 1 depicts an example intravascular volume status monitoring process for implementing the intravascular volume status monitor in accordance with an example.

FIG. 1 is a flow diagram depicting an example embodiment of an intravascular volume status monitoring process 100. It may be advantageous to monitor the intravascular volume status of a patient for any of a number of injuries or diseases such as cardiac arrest, burns, trauma including combat trauma, heart failure, sepsis, dehydration from any cause, renal failure, dialysis, etc. Further, it may also be advantageous to conduct general status monitoring including respiratory rate and respiratory quality monitoring as discussed herein. Further still, a longer term use of the process 100 may be to monitor the status of a patient suffering from edema. Prior to commencing monitoring, the testing apparatus, such as the testing apparatus 802 illustrated in FIG. 10 discussed below, would be applied to the patient (block 102). As described herein, the testing apparatus 802 may be any of a number of devices and sensors used to gather the venous volume and other data used to evaluate the patient's intravascular volume status.

Figure 2:
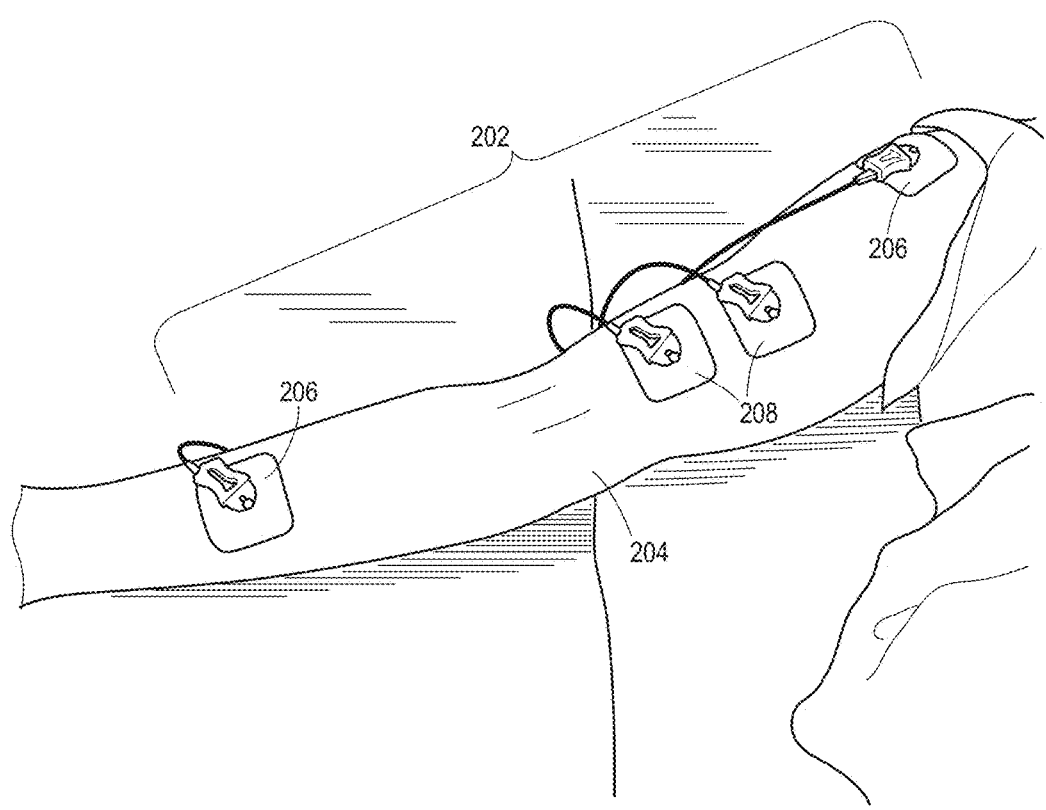
FIG. 2 depicts example placement of an impedance measuring device on an extremity of a patient (e.g., an arm), in accordance with an example application of the monitoring process of FIG. 1.

FIG. 2 is an illustration of how the testing apparatus 802 and the sensor(s) 816 operatively connected thereto may be used to measure impedance (and thus measure venous volume changes as discussed below). The testing apparatus 802 and the sensors 816 (not shown in FIG. 2) may collectively be referred to as an impedance measuring device 202. In some embodiments, the impedance measuring device is an impedance plethysmograph. The impedance measuring device 202 may be coupled to the patient via electrodes 206 and 208. As shown in FIG. 2, the electrodes 206 and 208 may be placed on the arm 204 of a patient. The impedance measuring device 202 may include two sets of electrodes. A first set of electrodes 206 are used to inject electrical current (e.g., 1 mA of alternating current) into the arm 204. A second set of electrodes 208 is used to monitor the impedance of the arm 204. Of course it will be appreciated that more than or less than four electrodes may be used to measure impedance. Further, different placement patterns for the electrodes 206 and 208 may be used (e.g., a circumferential pattern around the arm 204). Additionally, instead of placing the electrodes 206 and 208 on the arm 204, it will be understood that electrodes could be placed on the leg or neck of the patient to measure impedance as discussed herein. It will be appreciated that the electrodes 206 and 208 are placed peripherally (i.e., on the arm, neck, or legs) in order to take advantage of the venous volume modulation that will be produced through ventilation that will be reflected in relative blood volume changes in these peripheral sites. These sites are also insulated by distance so that they are not affected by motion of the chest. Traditional chest wall impedance used to measure respiratory rate use the impedance changes produced by small distance changes between impedance electrodes to make the respiratory rate measure. These changes in impedance at the chest are independent of cyclical blood volume changes. It will also be appreciated that the electrodes 206 and 208 do not have to be aligned along a vein. Volume changes are being made across a segment of tissue at the periphery which is dominated by movement of venous blood at that site. Accordingly, the testing apparatus 802 may be used to provide information about the relationship between ventilation, venous return, and heart function as described herein.

In another embodiment, the testing apparatus 802 may include any of a number of apparatuses useful for determining the volume of blood in one or more of the patient's extremities. For example, the testing apparatus may be a photoplethysmograph, a galvanic skin response monitor, a near infrared spectroscopy device, a laser Doppler device with our without speckle tracking, or an ultrasound device with or without speckle tracking. The present techniques, which focus on venous-side blood volume assessment, can be combined with other vascular techniques, including arterial-side measurement devices. As such, the testing apparatus 802 could be a device that also provides impedance cardiography, pulse pressure variation measurements, and stroke volume variation measurements, or the testing apparatus 802 could be a device coupled to one or more such devices (not shown), through a network, where such devices are coupled to a subject. Coordinating the present venous-side techniques with arterial-side measurements can provide additional information on vascular condition, such as preload, venous return, cardiac output, afterload, and vascular compliance.

As shown in FIG. 1, with the testing apparatus 802 in place, the monitoring of the patient's intravascular volume status may commence (block 104). Monitoring may be conducted at any of a number of physical locations (e.g., an intensive care unit, an operating room, a dialysis clinic, emergency department, ambulance, home health care, etc.). Once monitoring has begun, the testing apparatus 802 may take a first measurement of the extremity (block 106), that measurement being of a physical metric indicative of venous volume in the extremity. For example, if the testing apparatus 802 is an impedance measuring device such as the one illustrated in FIG. 2, the testing apparatus 802 may take a first impedance measurement of the extremity as the physical metric indicative of venous volume. The impedance of the extremity is based in large part on the blood volume within the extremity. Because blood is a good electrical conductor, impedance will decrease or increase if more or less blood volume, respectively, exists in the extremity. The first measurement may be a single data point, but the first measurement may also include multiple data points taken over a first period of time. Further, the first measurement may include a series of data points taken over a first period of time to establish a baseline measurement of the patient's intravascular volume cycle over the course of a plurality of respirations. As discussed herein, such respirations may be spontaneous and/or mechanically induced.

Subsequent to the first measurement of the extremity, an event causing blood to return to the heart via the venous system may occur (block 108). These events causing blood to return to the heart via the venous system may also be referred to as "respiratory challenges" herein. For example, taking a deep breath produces a larger negative intrathoracic pressure thus pulling more blood from the extremity. Spontaneous respiration creates negative pressure in the thorax which in turn creates a pressure gradient between the chest and the limbs/abdomen. This negative pressure gradient sucks blood into the large veins of the abdomen and chest which then empty this volume into the heart. Because spontaneous inspiration pulls blood from the extremities, the degree to which this will happen will depend on how full the right heart is and how forcefully the patient inspires. The degree to which spontaneous or negative pressure ventilation enhances venous return as it relates to central venous volume has been shown to be reflected by ultrasound imaging in the diameter of the inferior and superior vena cava and their ability to collapse. Similar but converse changes will be noted for patients undergoing positive pressure mechanical ventilation. In particular, the increase in intrathoracic pressure may cause the blood flow returning from the limbs and abdomen to slow, which may be detected by monitoring the change in volume as discussed herein. Centrally, this has been demonstrated using ultrasound imaging to change the diameter of the superior and inferior vena cava. It will be appreciated that such changes may be caused by higher intrathoracic pressures which in turn may cause expansion or collapse of the inferior and superior vena cava. Such expansion or collapse may change the volume of the inferior and superior vena cava and this in return will be manifest by volume changes peripherally. Because of this, the process 100 may be used to optimize vascular volume and even mechanical ventilation parameters by understanding the effects of mechanical ventilation on the central cardiovascular system's venous component. Additionally, changing the elevation of the extremities also may result in both local and remote blood volume changes that can be detected and are likely reflective of the patient's cardiovascular status as discussed herein. Raising the extremity will cause blood to flow into the central circulatory system, but the volume of blood flow will be dependent on the volume of blood already present in the central circulation system as well as the height of the extremity. Further, blood volume in the extremities may be affected by applying pressure to the patient's chest or abdomen. Accordingly, in an attempt to cause blood to return to the heart via the venous system, the patient may be instructed to take a deep breath, the patient may be instructed to inspire or expire against an impedance valve which produces a set negative inspiratory or positive expiratory pressure respectively, one or more of the patient's limbs may be raised or to a particular height, pressure (positive or negative) may be applied to the patient's chest or abdomen, and/or the parameters of positive pressure mechanical ventilation may be adjusted. The change in the volume of blood in the extremity being monitored may be used to determine the patient's intravascular health similar to changes in IVC diameter. In fact changes in IVC diameter as measured by ultrasound during respiration (spontaneous and mechanical ventilation) have been accurately correlated with right atrial or central venous pressure. FIGS. 8 and 9 demonstrate quantifiable changes in limb impedance and changes in vena cava diameter. In essence the limbs or neck would be treated as extensions of the vena cava, such that one can determine changes in blood volume in the limbs or neck as well as the volume and diameter changes in the vena cava, from changes in impedance in limbs or neck. These determinations can be explicit, e.g., with actual volumetric or length units, or inferred, e.g., maintaining units as impedance units. In this way, measure of changes in impedance, or other physical metric, may be used to determine changes in blood volume on the heretofore unmeasured venous-side of the vascular system. Moreover, the changes in blood volume may be determined, explicitly from the impedance data or inferentially as represented by the impedance data. Moreover still, the changes in limb or neck volume, as measured by impedance or other method, also correlate with changes in right atrial pressure and central venous pressure.

During and/or after the occurrence of the event causing modulation of blood return to the heart via the venous system, the testing apparatus 802 may take a second measurement of the extremity (block 110), for example, of the same physical metric indicative of venous volume in the extremity as first measured (block 106). For example, if the testing apparatus 802 is an impedance measuring device such as the one illustrated in FIG. 2, the testing apparatus 802 may take a second impedance measurement of the extremity. As with the first measurement, the second measurement may include a series of data points taken during a second period of time. Using the first measurement and the second measurement, the process 100 may then determine the change in venous volume in the extremity (e.g., by subtracting the mean value of the first measurement from the mean value second measurement) (block 112). The block 112 may determine the change in venous volume from the values of the physical metric (e.g., impedance) taken at the first (block 106) and the second (block 110) points in time. When impedance (also termed bioimpedance) is used as the physical metric, then the changes in impedance will provide a relatively linear correlation to the changes in volume when compared to the changes in the diameter of the vena cava. In some examples, the actual change in blood volume is determined from the changes in impedance, i.e., calculated, while in other examples, the change is determined inferentially. Thus, in these ways, the present techniques are, in some implementations, able to determine changes in venous blood volume without needing to measure absolute values for the physical metric, e.g., without needing to measure absolute impedance. Instead changes in the physical metric, e.g., changes in impedance, can be measured.

In some examples, the blocks 106 and 110 may take the first and second measurements, respectively, over a period of time and determine a local peak value of the physical metric over those periods of time value, and provide those local peak values to the block 112. In some examples, the blocks 106 and 110 may take the first and second measurements, respectively, over a period of time and determine a peak-to-peak value for the physical metric over those periods of time, and provide those peak-to-peak values to the block 112. In any of these examples, the first and second measurements may be normalized to each individual's breathing baseline. In some examples, the normalization can occur from plotting this data versus changes in the diameter of an individual's inferior vena cava. In an example experimental implementation using control subjects and patients who were critically ill, an exponential model was fit to measured impedance data and was shown to have high predictive value of impedance changes on both a per individual basis (e.g., $R^2=0.91\pm0.05$ and $R^2=0.96\pm0.03$ for control subjects and patients, respectively) and a per subject group basis.

Referring again to FIG. 1, the process of taking measurements of volume before and after a blood moving event and calculating the change in volume may be repeated one or more times. That is, the processes for blocks 106-112 may be repeated numerous times to monitor and assess the effects of different events on blood volume. Additionally various types of blood moving events may occur during monitoring. For example, a patient may be instructed to breathe normally for several cycles, instructed to take several deep breaths, and then have a limb be raised and/or lowered as discussed herein. By monitoring the patient's intravascular volume status before and after several occurrences of events causing blood to return to the heart via the venous system, a healthcare provider may assess whether the addition or subtraction of intravascular fluid would be advantageous to the patient's health as discussed below. The length of time the patient may be monitored may vary and may depend in part on (a) how ill or injured the patient is and (b) what treatments are being undertaken to optimize the patient's cardiovascular system and how the patient's cardiovascular system responds to this treatment discussed below. Accordingly, the patient may be monitored for minutes, hours, or days. Further, it may be advantageous to continuously monitor the extremity to detect changes in circulating volume over time in order to detect hydration states and continuing blood loss.

The event(s) modulating blood return may result from direct or indirect instruction from health care personnel, and as part of a treatment efficacy determination. Example events include spontaneous inspiration, positive pressure mechanical ventilation, raising a limb or extremity or neck of the patient, applying negative or positive pressure to the abdomen or chest, inspiration against a negative impedance valve, or discrete maneuvers performed with mechanical ventilation. Those discrete maneuvers performed with mechanical ventilation may include, by way of example, adjusting positive pressure ventilation, negative pressure ventilation, maintaining inspiratory or expiratory pause, or a combination thereof.

Personnel may instruct patients to engage in events modulating blood return, at, before, or during a diagnosis test or administration of treatment. The change in venous blood volume is then determined based on changes in measured impedance before and after the events. The personnel may instruct the patient to engage in one event or in a protocol of events, e.g., performing different breathing exercises in a prescribed manner (such as, rapid breaths followed by deep expiration and deep inspiration breaths, different types of breaths taken at different limb positions, etc.). For example, an administering physician may instruct a patient to perform a blood-modulating event, from which changes in venous blood volume is determined between different time points, to determine how the patient will hemodynamically respond to treatment by a cardiovascular fluid, or how the patient will respond to the removal of a cardiovascular fluid. The physician thus uses the blood-modulating events to assist in determining patient's likely responsiveness a treatment. From here, the physician can assess which treatments will be most effective. The technique can be used to determine responsiveness to any number of conditions, including hemodynamic responsiveness to administration or removal of one or more cardiovascular drugs, such as drugs intended to promote cardiac output, changes in cardiovascular preload, changes in cardiovascular afterload, etc. In yet other examples, the blood modulating events may be used to determine how a patient will respond to changes in mechanical or noninvasive ventilation.

Mechanical ventilation may be from adjusting positive pressure ventilation, negative pressure ventilation, maintaining inspiratory or expiratory pause, or a combination thereof.

In some examples, instructions for performing blood modulating events may be supplied to the patient automatically by a system 800, for example, using a display 826, and under instruction by instructions executed by a processor 808 and stored in a program memory 806, described further hereinbelow.

The instructions can be provided to a patient that is remote from a medical facility connected to the testing apparatus through a network, such as at the patient's home. Whether at a medical facility or remotely, the technique may be performed on a patient undergoing a general examination or undergoing a specific treatment, such as treatment for cardiac arrest, edema, burns, trauma, heart failure, sepsis, dehydration, renal failure, or dialysis.

FIGS. 3-7 illustrate graphs of the impedance measured in an extremity before, during, and after the occurrence of the event causing blood to return to the heart via the venous system (e.g., spontaneous respiration, moving one or more limbs, etc.). Each of FIGS. 3-7 includes three graphs. As discussed below, the top graph in each of FIGS. 3-7 is a graph of the impedance measured at an extremity of the patient (e.g., arm, leg, etc.). The middle graph in each of FIGS. 3-7 is a graph of the impedance measured at the chest wall of the patient. The electrodes were placed in a pattern similar to patterns used in known in-hospital respiratory monitoring. However, unlike the impedance measured at the patient's extremity, the changes in impedance in the chest level does not represent blood volume changes in the chest but rather changes in the distance between the electrodes in response to chest expansion. It will be appreciated by one of ordinary skill in the art that in each of FIGS. 3-7, a comparison of the top graph of impedance measured at an extremity to the middle graph of impedance measured at the chest wall shows the greater sensitivity conferred by the methods discussed herein. In particular, the top graph may illustrate a more pronounced response to respiratory challenges relative to regular, spontaneous breaths. The bottom graph in each of FIGS. 3-7 is a graph of the end-tidal $CO_2$ monitoring from the nose. End-tidal $CO_2$ is a direct measurement of respiration, however the measuring apparatus used to generate FIGS. 3-7 introduced a slight delay in registering the measurements, which caused the bottom graph to be slightly out of phase with the top and middle graphs due to the side-stream sampling nature of the $CO_2$ measurement. However, because the amplitude and frequency of the top graph of impedance track with the peaks and troughs of the bottom graph of end-tidal $CO_2$, it will be appreciated by one of ordinary skill in the art that measuring impedance at an extremity can serve as an indirect measurement of respiratory rate and the degree of respiratory effort. The performance of impedance in this aspect is improved over end-tidal $CO_2$ monitoring.

Figure 3:
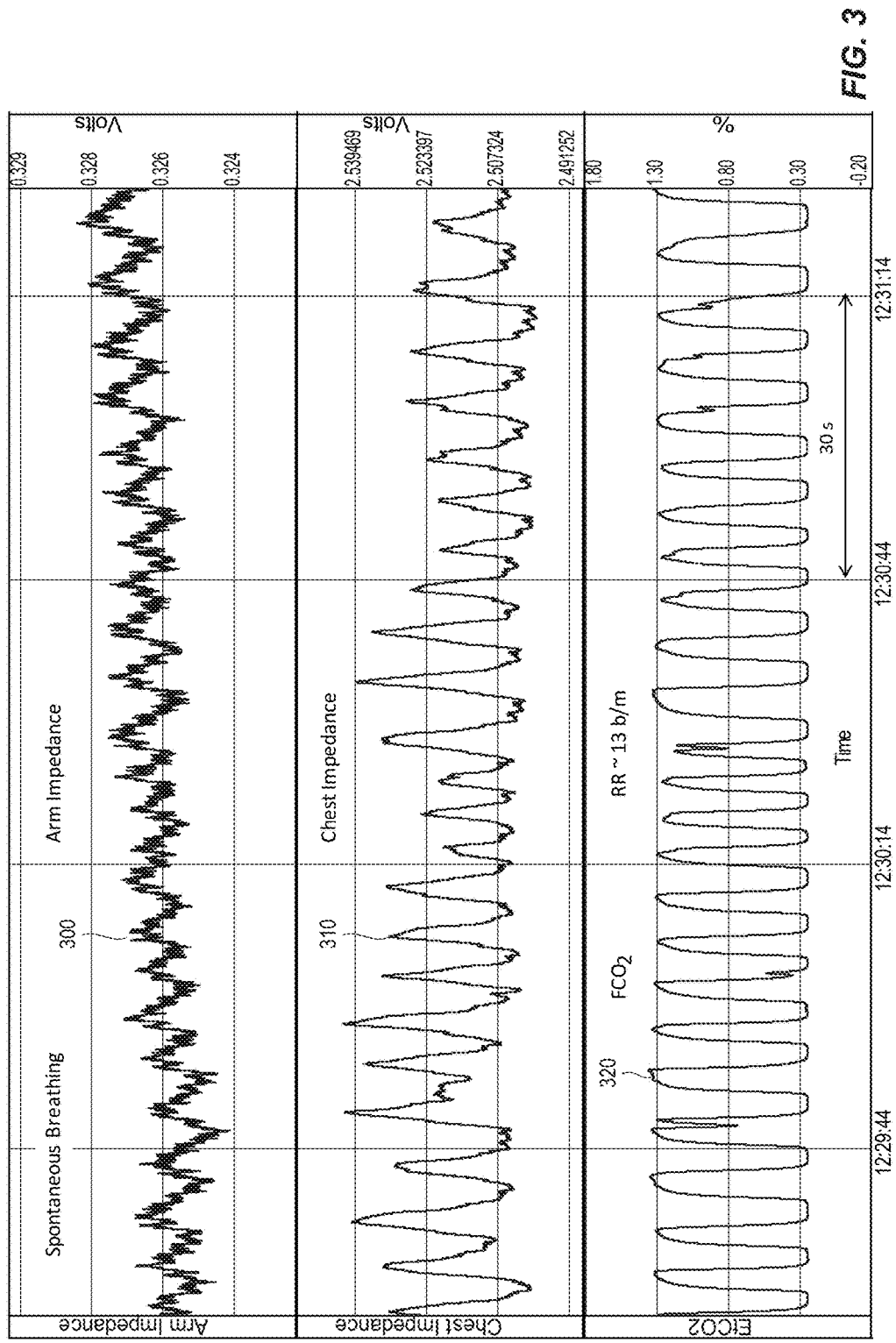
FIGS. 3-7 depict example graphs of impedance measured from an arm of a patient, impedance measured from the chest wall of the patient, and end-tidal carbon dioxide ($CO_2$) measured from the nose of a patient as functions of time.
Figure 4:
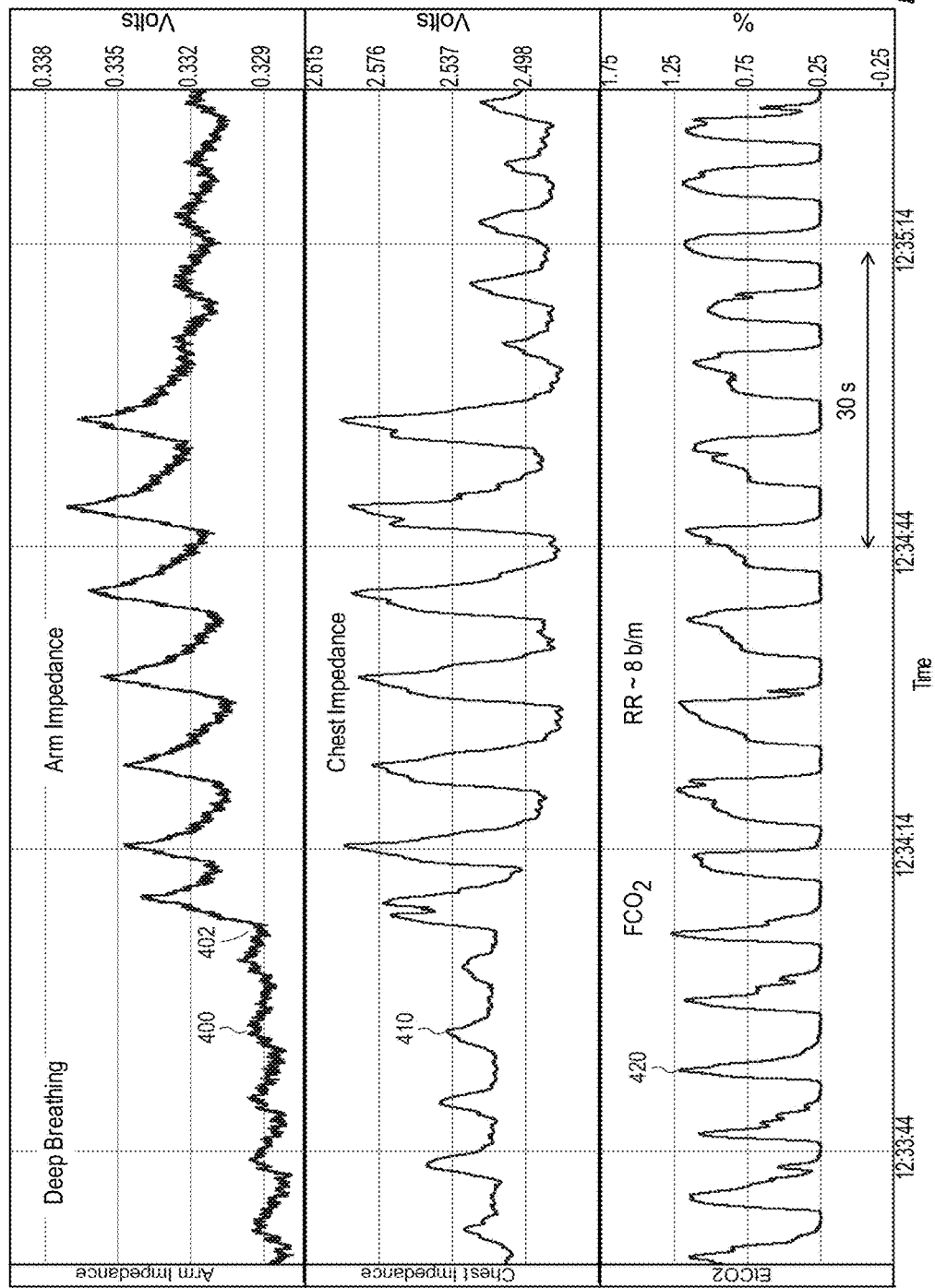
Figure 5:
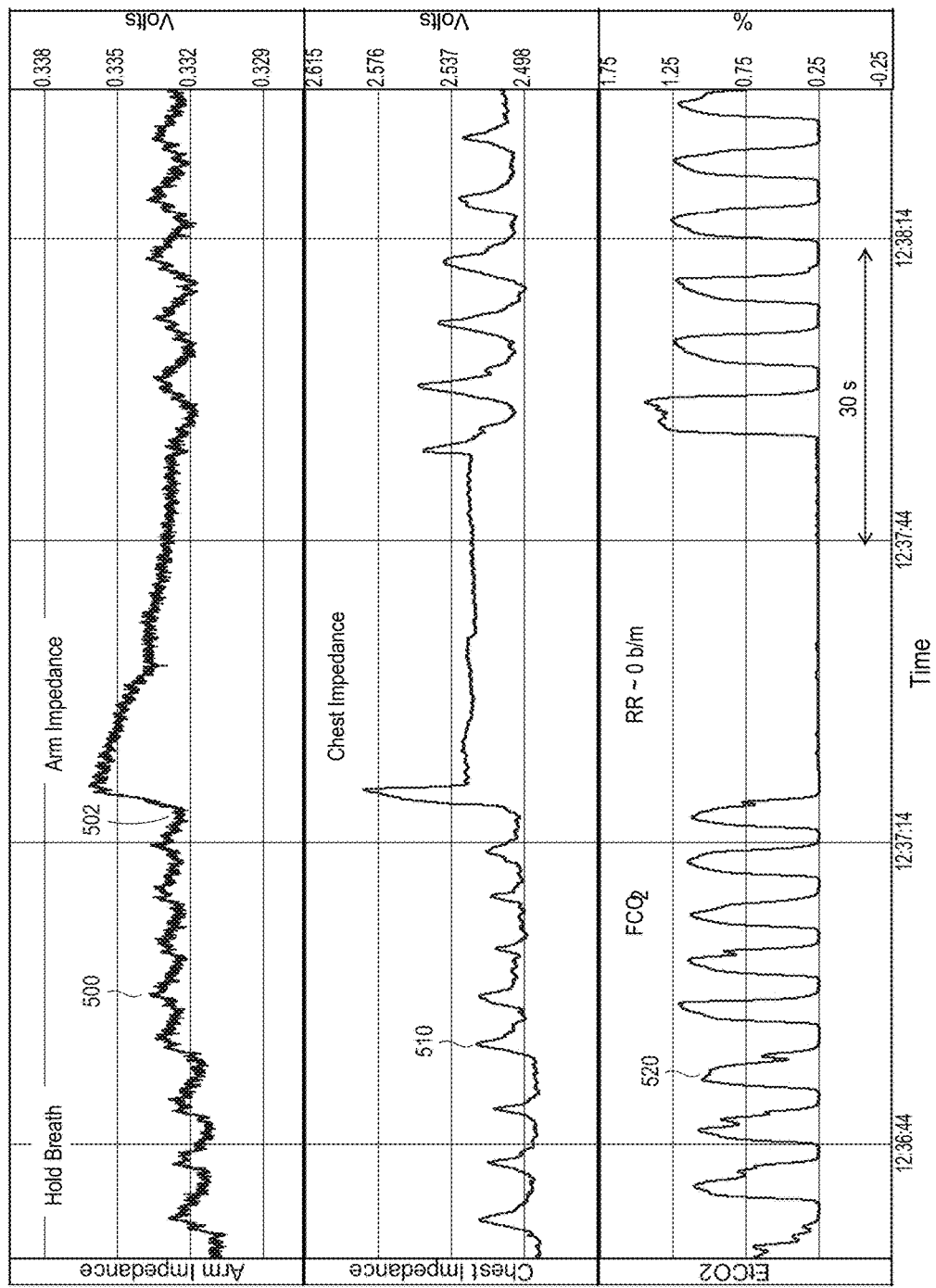

FIG. 3 includes an illustration of a graph 300 of the impedance measured in a patient's arm while the patient engages in normal, spontaneous breaths. FIG. 3 also includes a graph 310 of chest impedance and a graph 320 of end-tidal $CO_2$. It will be appreciated that each of the graphs 300, 310, and 320 track one another and exhibit a substantially-regular amplitude and frequency as the patient breathes. FIG. 4 is an illustration of a graph 400 of the impedance measured in a patient's arm while the patient engages in deep, spontaneous breaths starting at point 402. FIG. 4 also includes a graph 410 of chest impedance and a graph 420 of end-tidal $CO_2$. It will be appreciated that amplitude of waveform of the graphs 400 and 410 increase after point 402 while the patient is taking deep breaths, however the rate of breathing has not substantially increased. Additionally, it will be appreciated that the frequency of the graphs 400, 410, and 420 have not increased. Additionally, FIG. 5 is an illustration of a graph 500 of the impedance measured in a patient's arm while the patient takes and holds a deep breath at point 502, with a characteristic spike and gradual tapering of impedance. FIG. 5 also includes a graph 510 of chest impedance and a graph 520 of end-tidal $CO_2$. As discussed herein, the relatively larger change in impedance may indicate a greater flow of blood toward the heart caused by greater negative intrathoracic pressure caused by a deep breath. The differences between FIG. 3 and FIGS. 4 and 5 will be appreciated by one of ordinary skill in the art. In particular, it will be noted that the change in impedance in FIG. 4 and FIG. 5 while the patient was taking deep breaths or taking and holding a deep breath, respectively, are larger relative to the change in impedance in FIG. 3.

Figure 6:
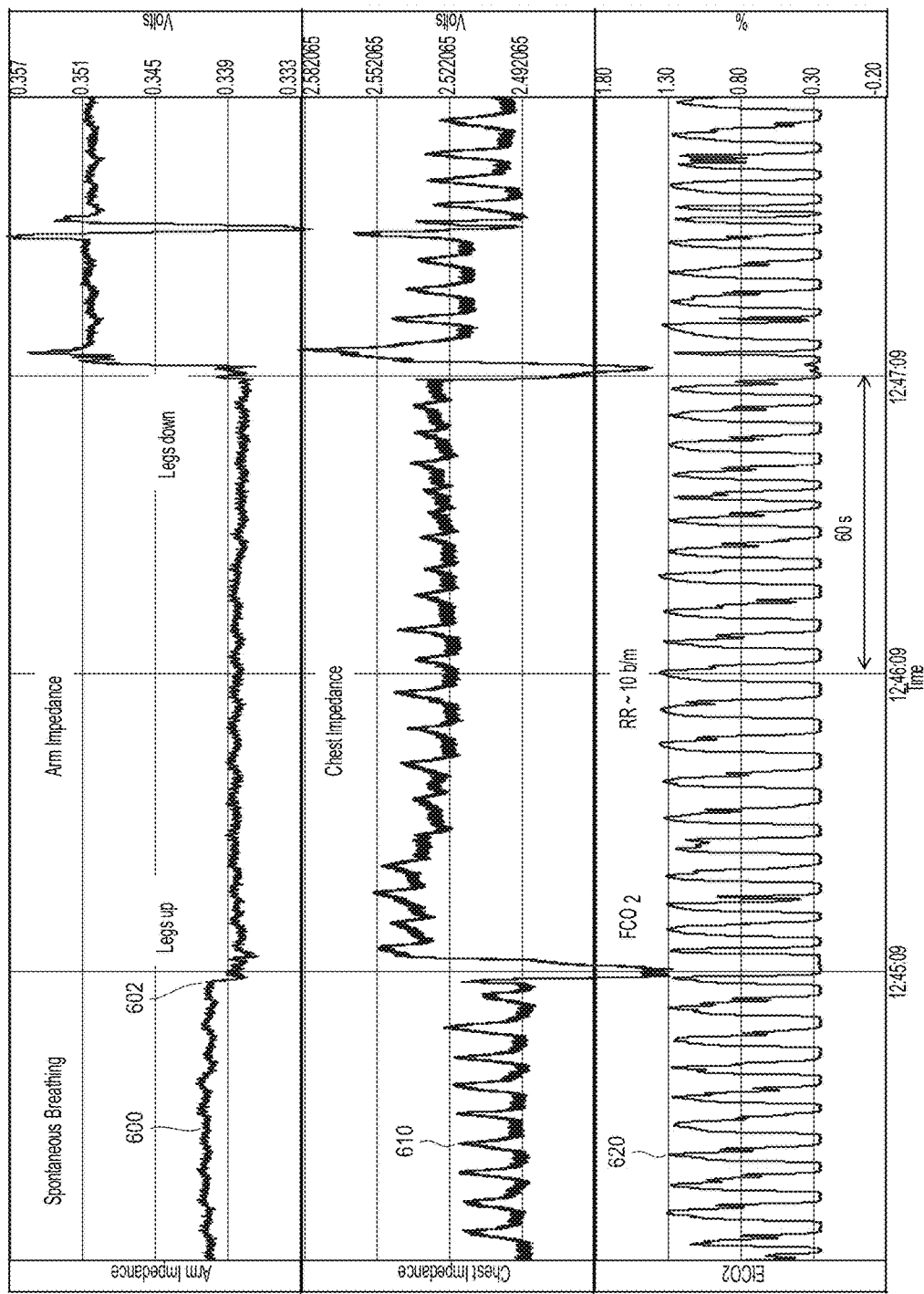
Figure 7:
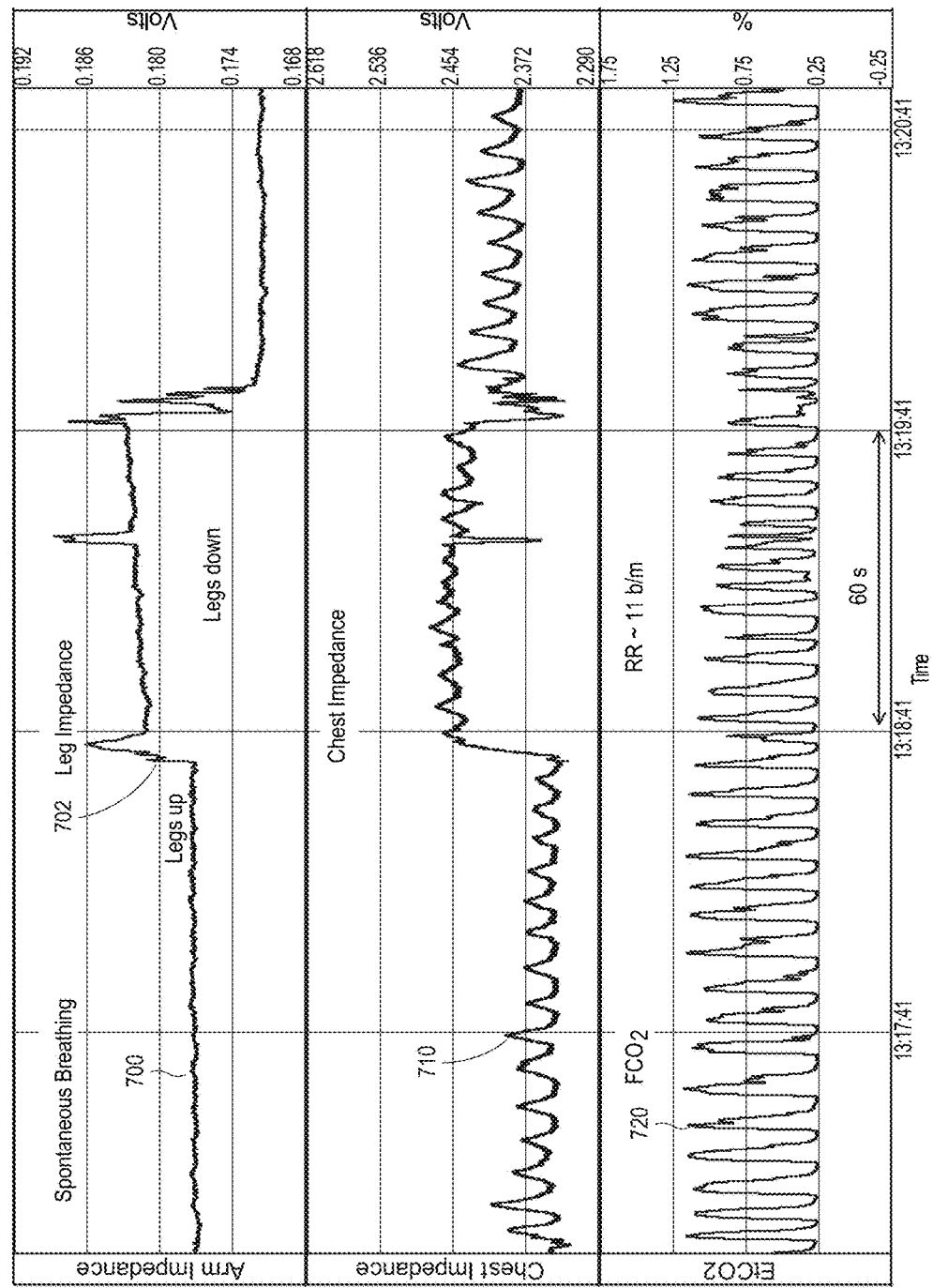
Figure 8A:
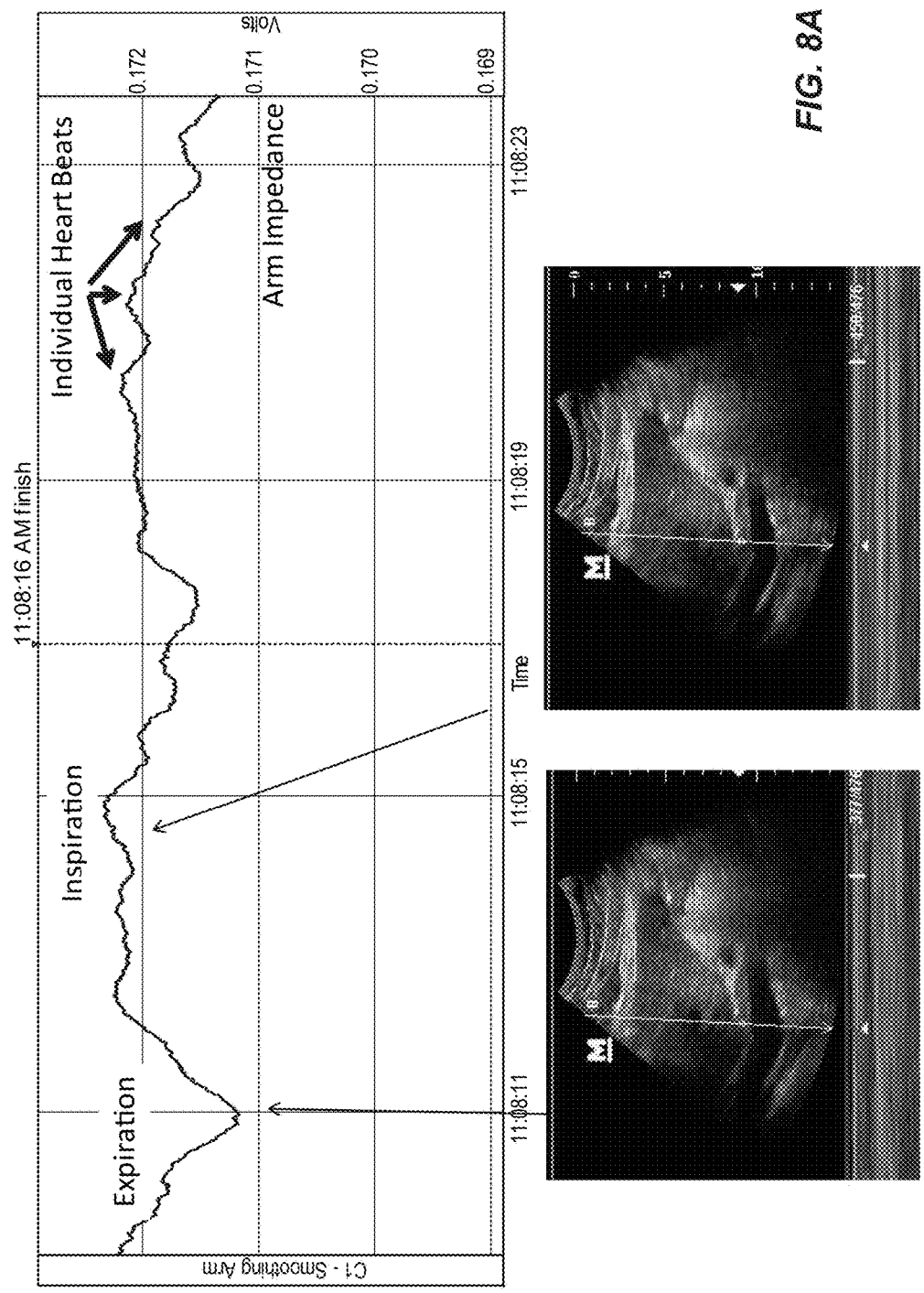
FIGS. 8A-8D depict graphs of arm impedance measurements measured under different breathing conditions, specifically, normal breathing (FIG. 8A), deep breathing (FIG. 8B), holding breath (FIG. 8C), and sniff breathing against a partially closed glottis (FIG. 8D). Simultaneous changes in IVC diameter are also noted.
Figure 8B:
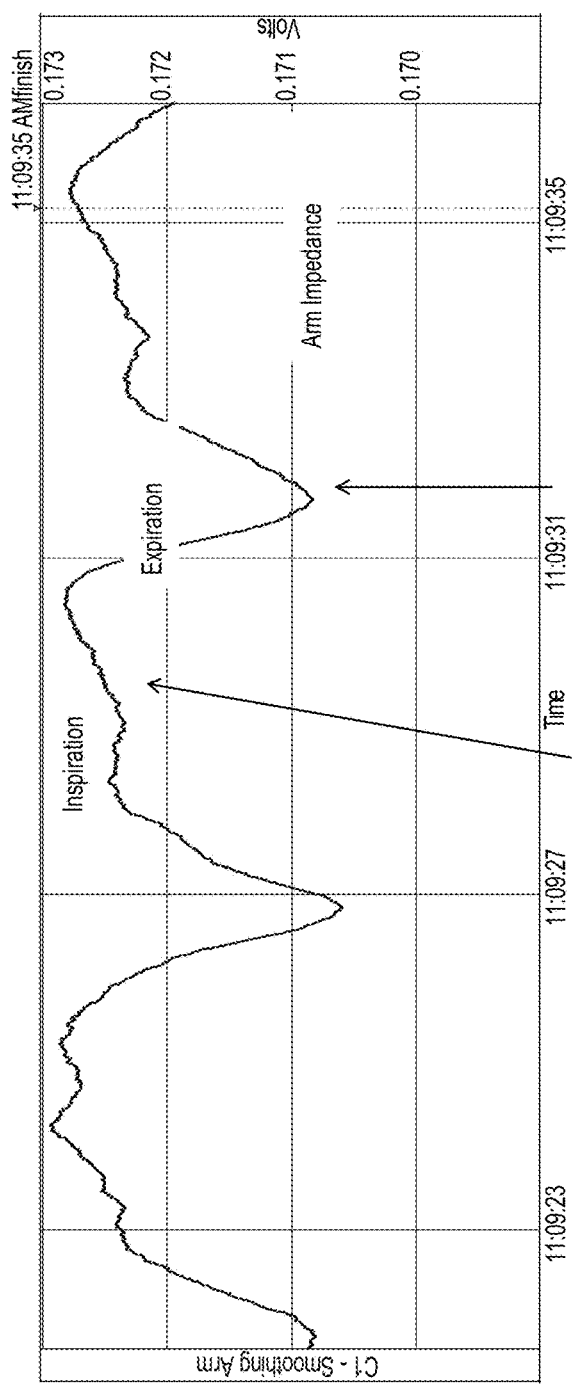
Figure 8B:
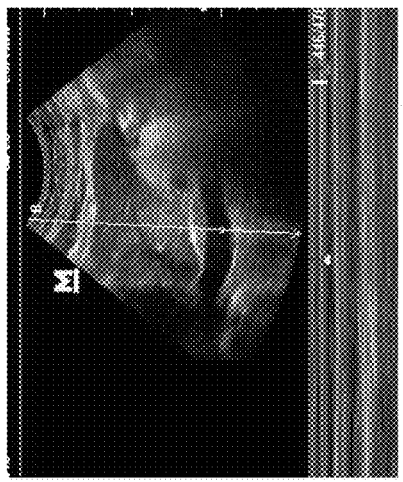
Figure 8B:
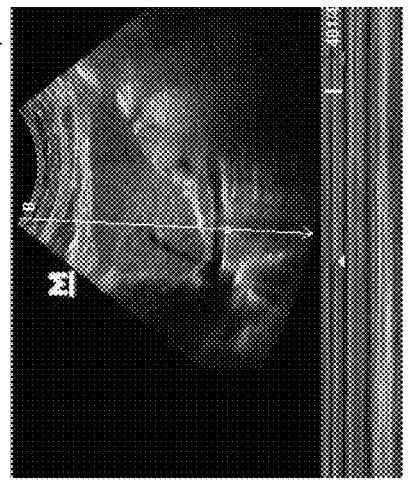
Figure 8C:
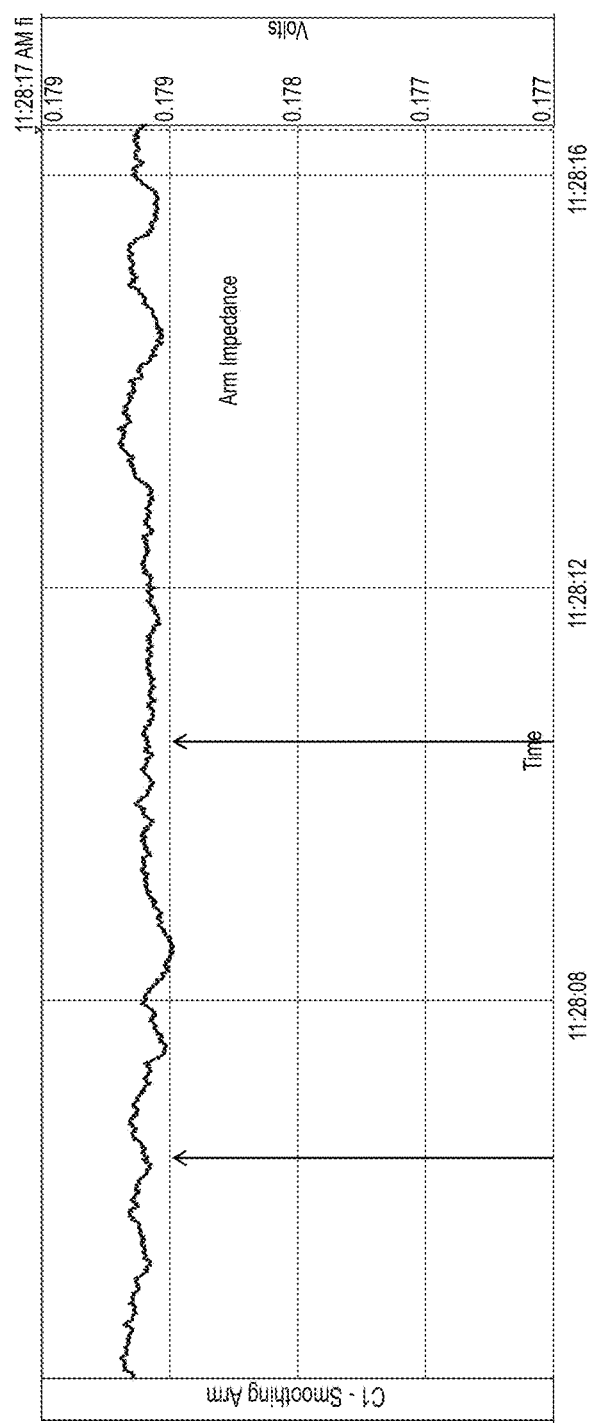
Figure 8C:
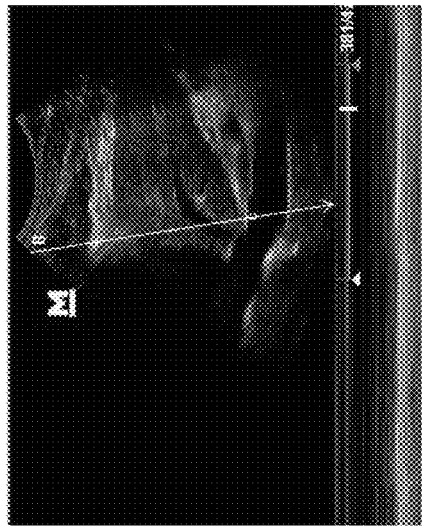
Figure 8C:
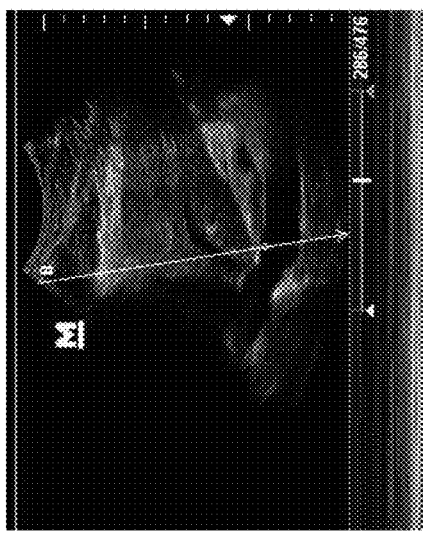
Figure 8D:
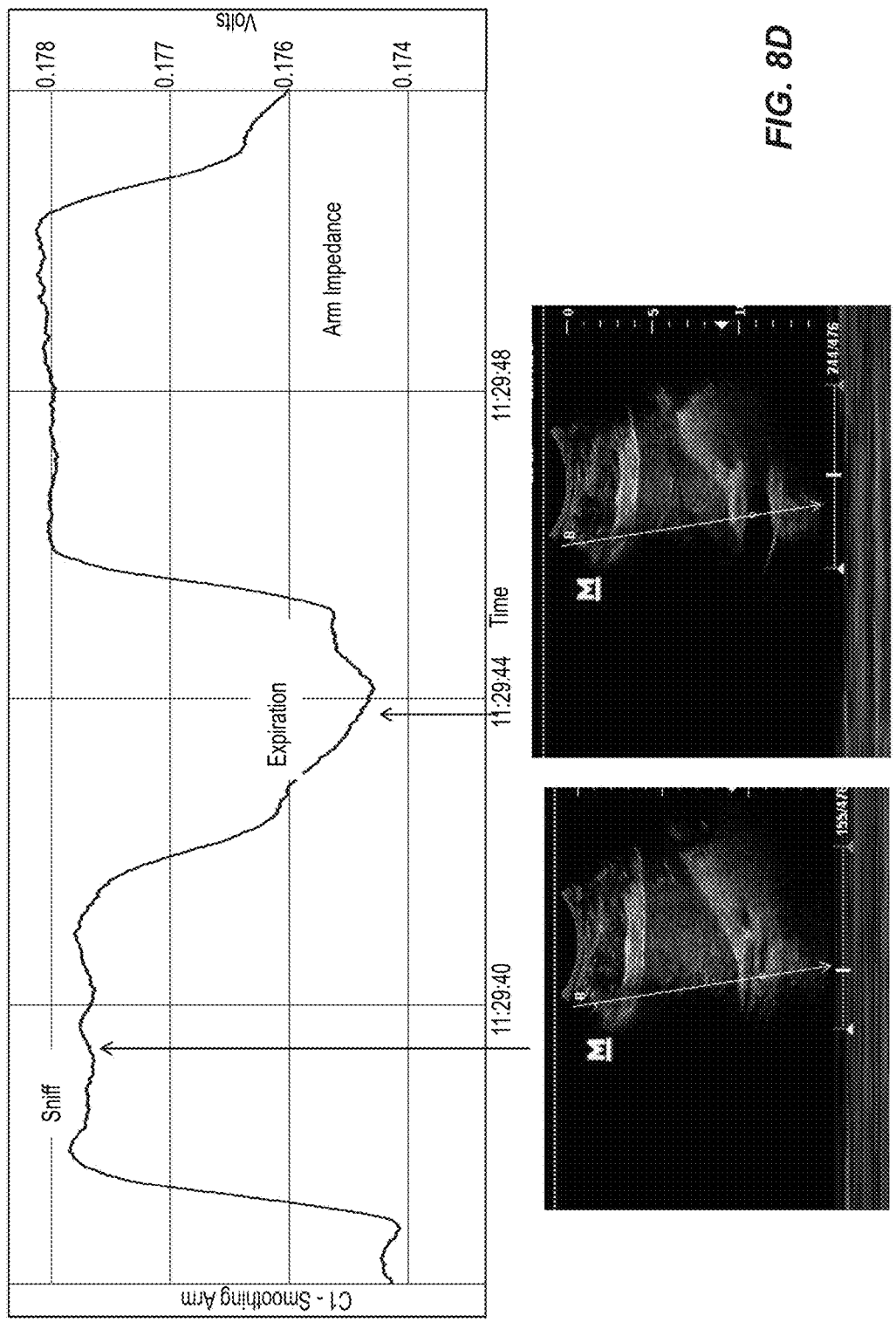
Figure 9A:
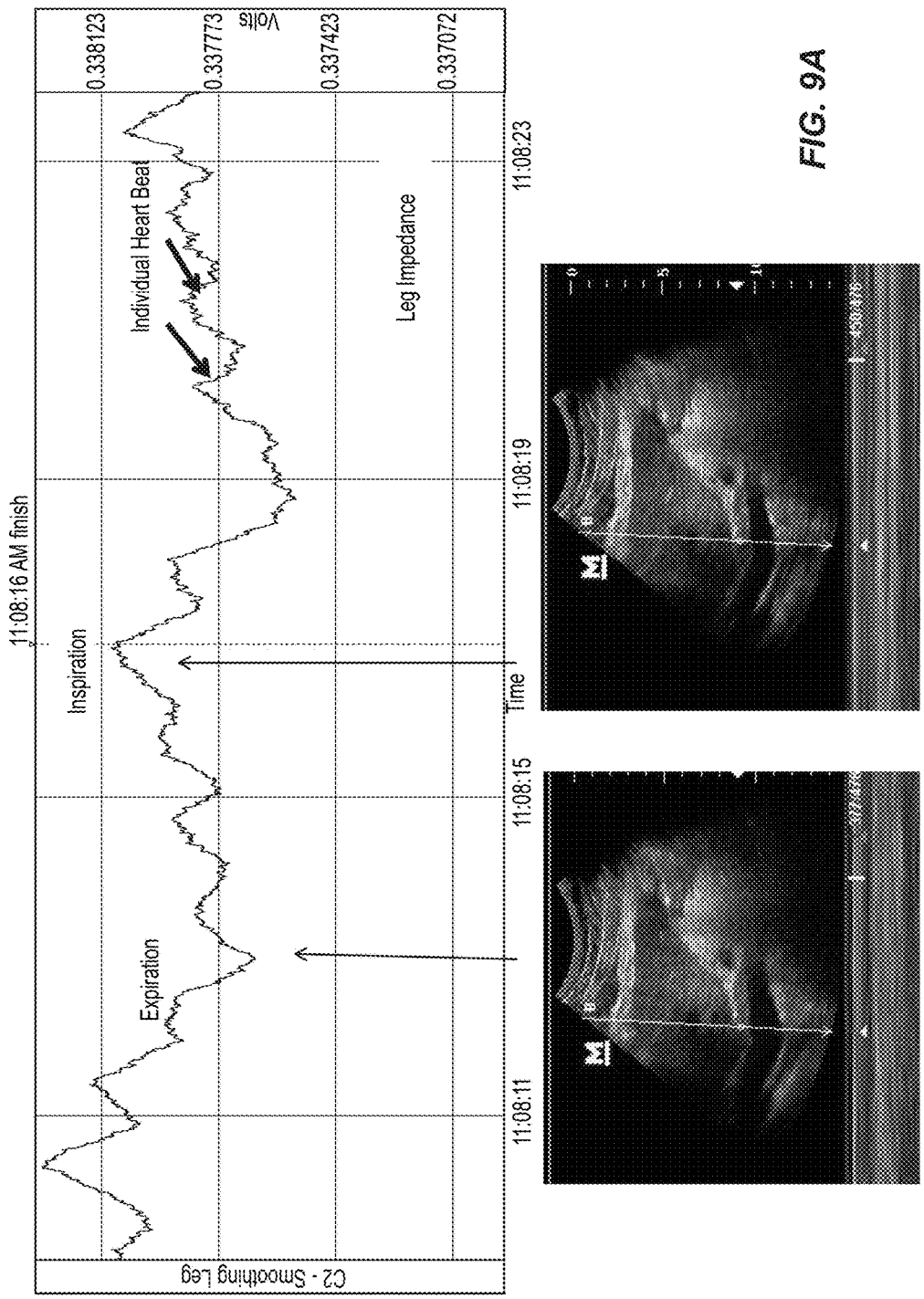
FIGS. 9A-9D depict graphs of leg impedance measurements measured under different breathing conditions, specifically, normal breathing (FIG. 9A), deep breathing (FIG. 9B), holding breath (FIG. 9C), and sniff breathing against a partially closed glottis (FIG. 9D). Simultaneous changes in IVC diameter are also noted.
Figure 9B:
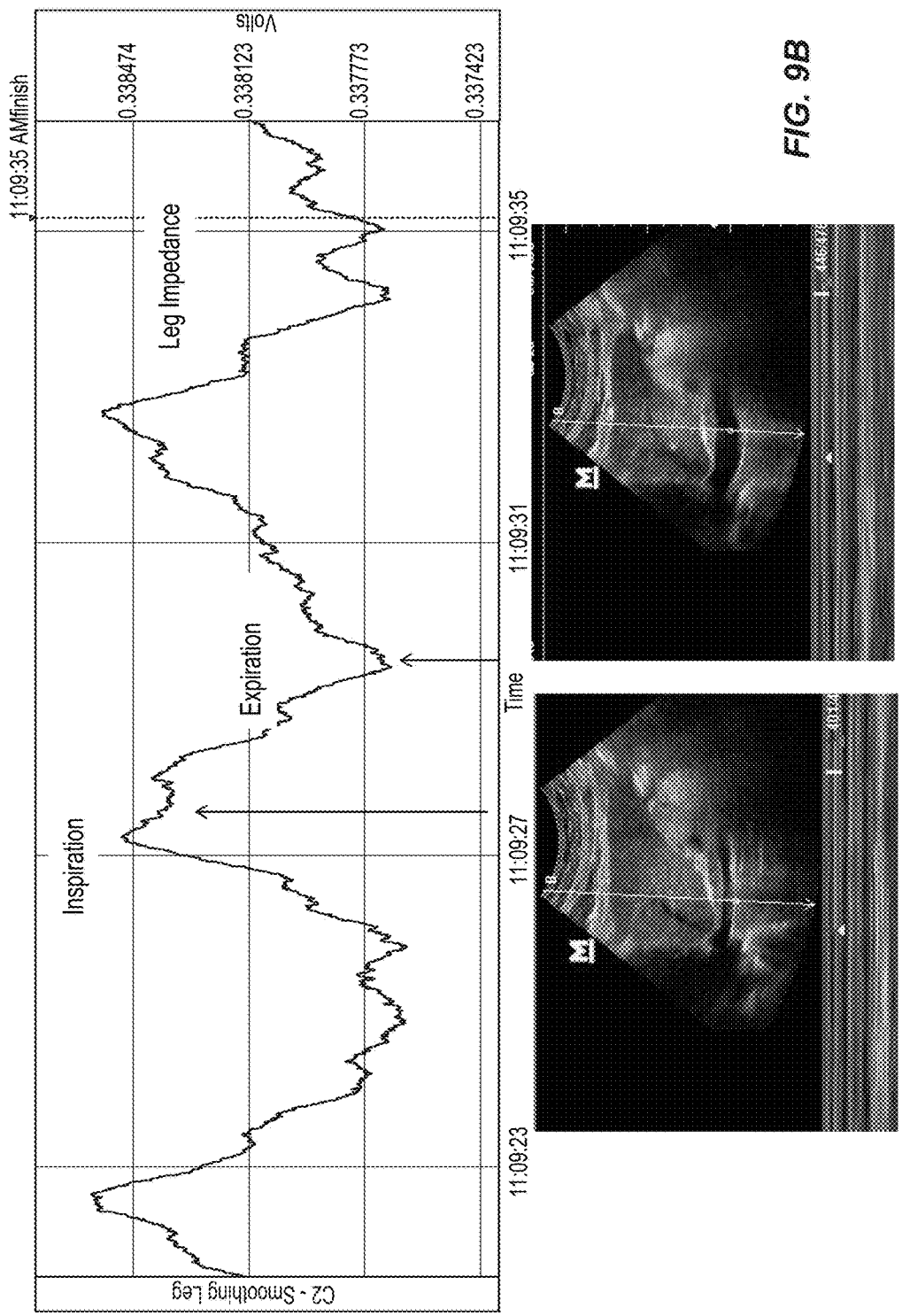
Figure 9C:
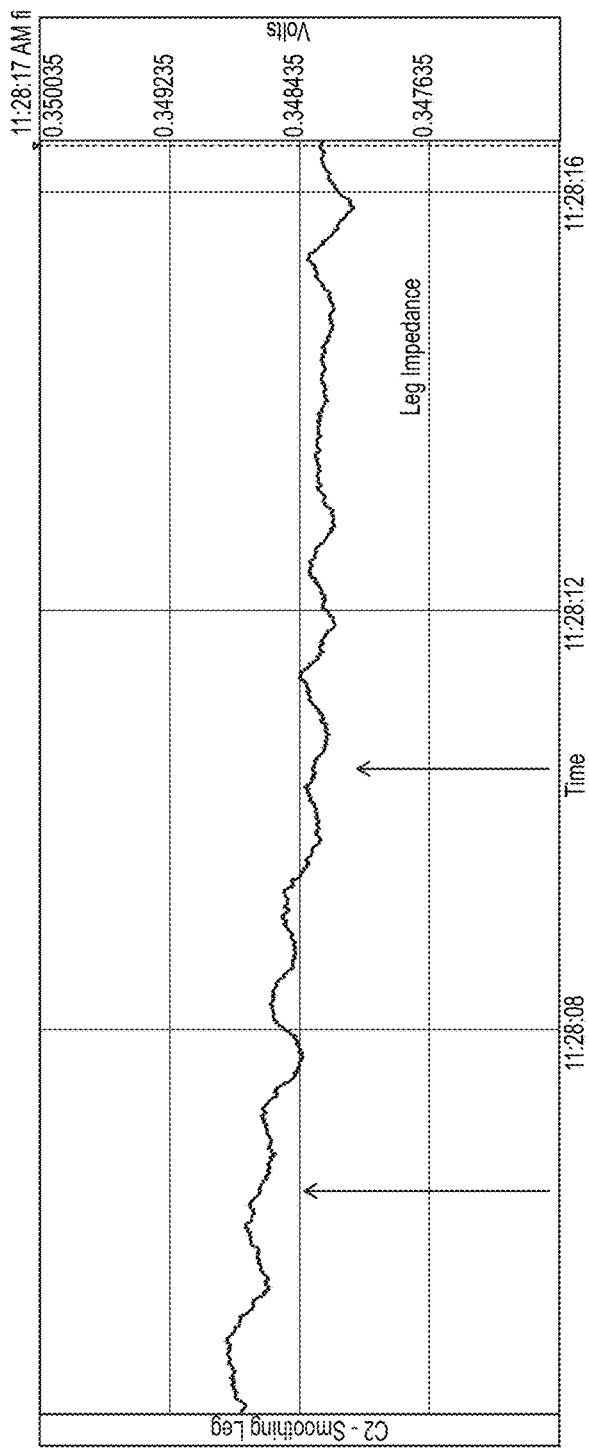
Figure 9C:
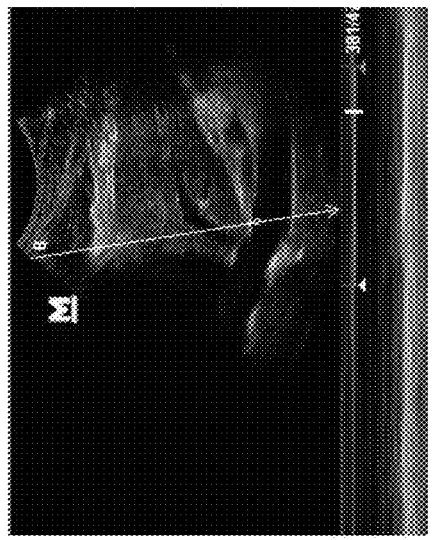
Figure 9C:
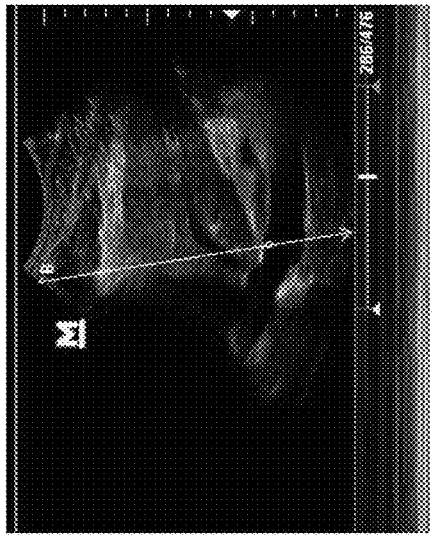
Figure 9D:
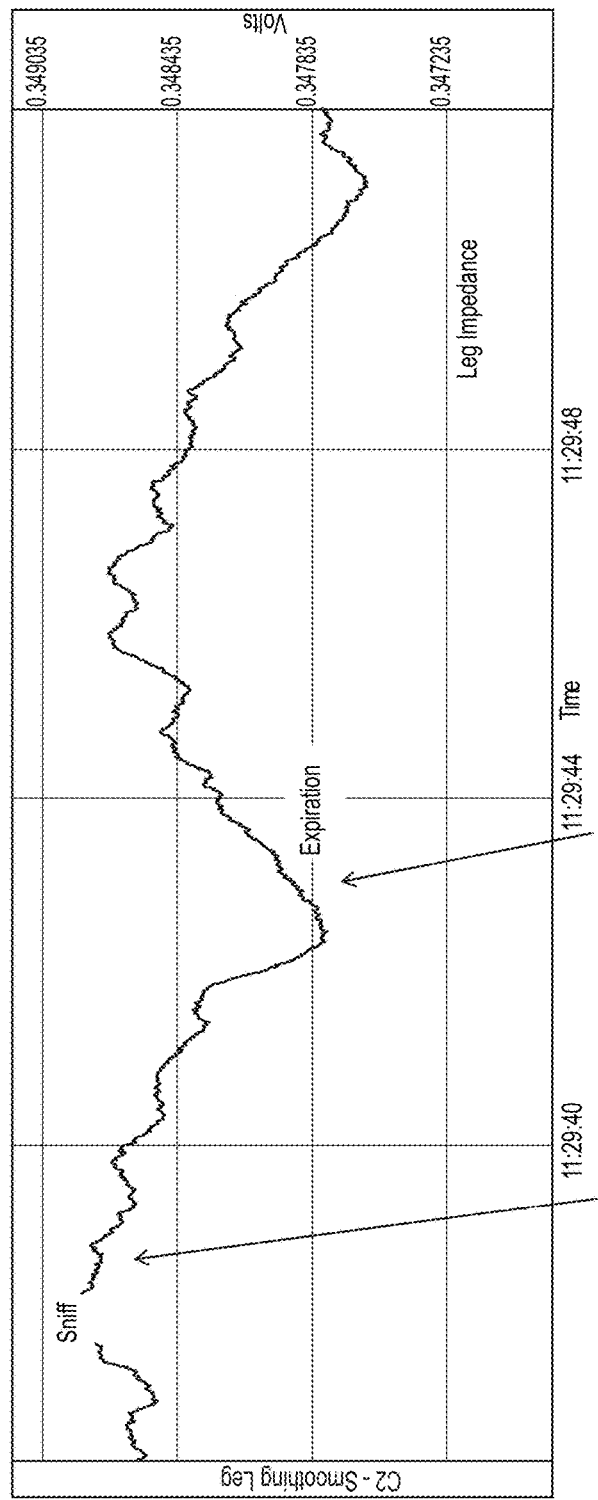
Figure 9D:
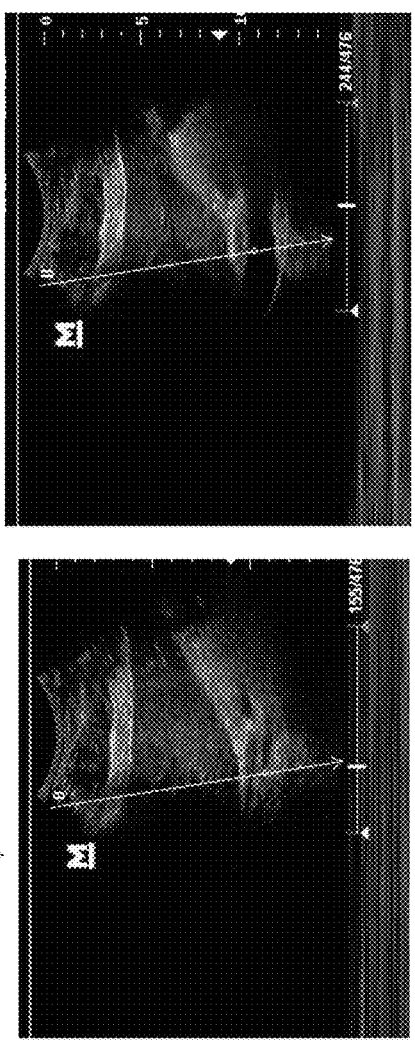

FIG. 6 is an illustration of a graph 600 of the impedance measured in a patient's arm while the patient's legs are raised and lowered while the patient is taking spontaneous breaths. At point 602, the patient's legs are raised, causing the impedance measured in the arm to decrease slightly as more blood is present in the patient's arm. Then, at point 604, the patient's legs are lowered, causing impedance in the arm to spike as less blood is present in the patient's arm. FIG. 6 also includes a graph 610 of chest impedance and a graph 620 of end-tidal $CO_2$. FIG. 7 is an illustration of a graph 700 of the impedance measured in a patient's leg as the patient's legs are raised and lowered while the patient is taking spontaneous breaths. At point 702, the patient's legs are raised, causing the impedance measured in the leg to increase as less blood is present in the leg. Then, at point 704, the patient's legs are lowered, causing the impedance measured in the leg to decrease as more blood is present in the patient's leg. FIG. 7 also includes a graph 710 of chest impedance and a graph 720 of end-tidal $CO_2$.

Referring again to FIG. 1, after calculating the change in venous volume at the extremity, the cardiovascular health of the patient can be evaluated and appropriate treatments or interventions may be planned and applied (block 114). A healthcare provider may use the process 100 to assess the condition of the patient to determine whether it may be beneficial to increase the volume of circulating blood in order to achieve optimum cardiovascular circulation or output. If the patient is volume deficient, the volume of circulating blood may be increased, for example, by a blood transfusion, administering intravenous (IV) fluids, or other known ways of administering fluids. If the patient is hypervolemic, the volume of circulating blood may be decreased, for example, by diuresis or other known ways of decreasing fluids. In the past, a healthcare provider might hypothesize that a patient is volume depleted based merely on the patient's injury or illness (e.g., severe burns) and administer IV fluids without having the capability of determining whether such fluids may be beneficial beforehand. However, using the disclosed embodiments, if a healthcare provider initially believes that a patient has a condition that would be respond favorably to the addition of IV fluids, but the change in volume (e.g., as determine by measuring the change in impedance as discussed herein) is small in response to various respiratory challenges (e.g., deep breaths, manipulation of limbs, etc.), then the healthcare provider may determine that the patient will not respond to being given additional IV fluids. Conversely, if the change in volume is large, then the healthcare provider may determine that the patient will respond favorably to fluids. Similarly, if the healthcare provider hypothesizes that the patient's condition may be improved by removing fluids, the healthcare provider may use the example process 100 to determine that the change in volume is small, indicating that removing fluids may be beneficial. Additionally, the process 100 may be used to titrate positive pressure or negative pressure ventilation and the administration of either pharmaceuticals or mechanical maneuvers that increase blood flow dependent or independent of making the heart pump more efficiently.

Further, it is possible to use the technology as a respiratory monitor to determine not only the respiratory rate but also the degree of respiratory effort. Accordingly, the process 100 may be used to estimate central venous pressure (CVP) levels noninvasively similar to how Ultrasound of the superior or inferior vena cava have been used, as well as to detect changes in the cardiorespiratory system which may signal the deterioration or improvement of a patient's condition. Because there are no valves in the proximal large veins in the neck and limbs, the geometric changes in these vessels in response to the respiratory challenges discussed above may parallel those of the superior and inferior vena cava. Accordingly, the volume measuring techniques discussed above may be useful for indirectly measuring the volume of blood in the superior and inferior vena cava.

Figure 10:
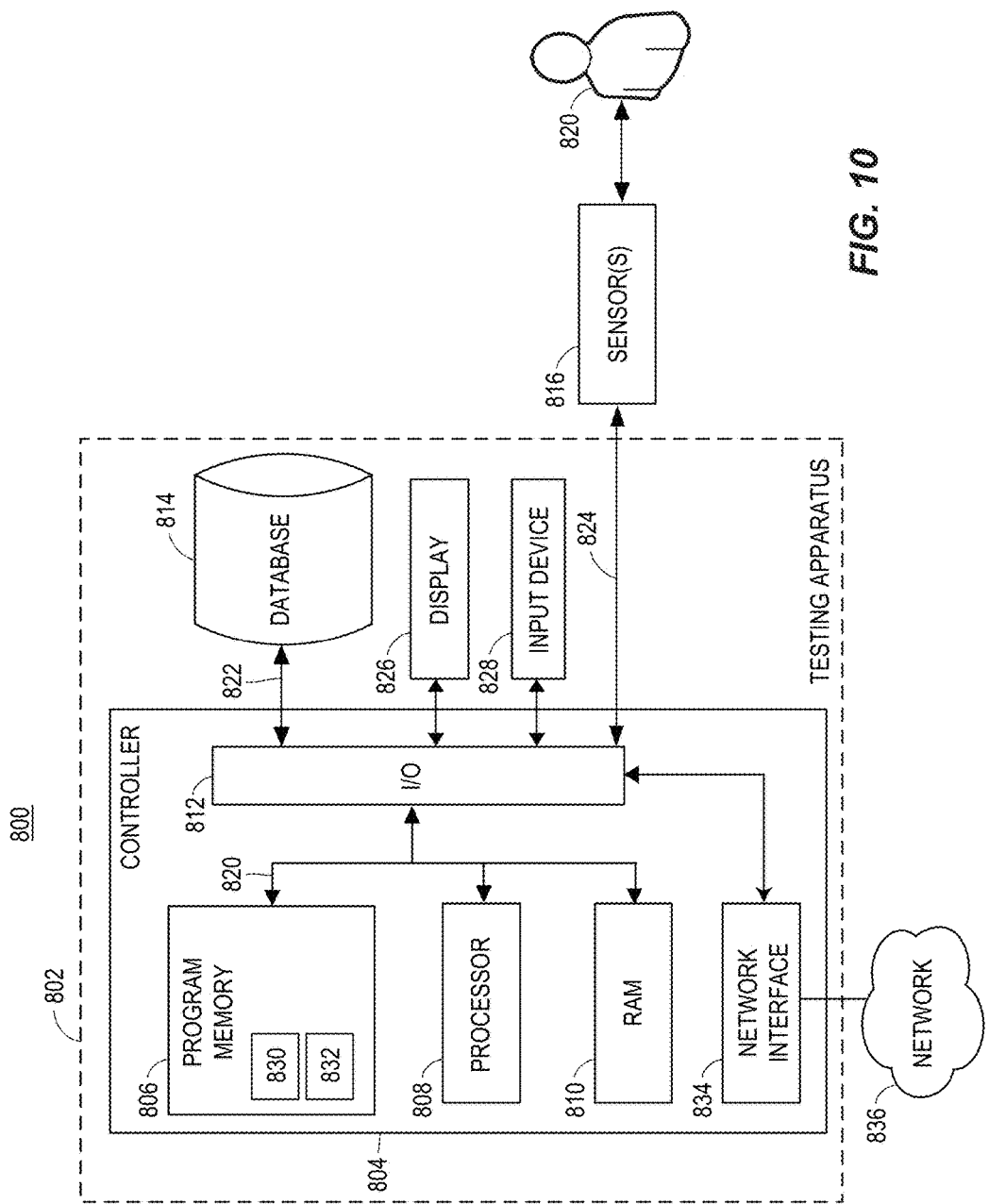
FIG. 10 depicts an example block diagram illustrating the various components used in implementing an exemplary embodiment of the intravascular volume monitoring method.

FIG. 10 is an example block diagram 800 illustrating the various components used in implementing an example embodiment of the intravascular volume monitoring process 100 discussed herein. A testing apparatus 802 may be coupled to a patient 820 via sensors 816 in accordance with executing the functions of the disclosed embodiments. The testing apparatus 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, the processor 808 (may be called a microcontroller or a microprocessor), a random-access memory (RAM) 810, and the input/output (I/O) circuit 812, all of which are interconnected via an address/data bus 820. It should be appreciated that although only one microprocessor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824 may operatively connect the controller 804 to a sensor 816 through the I/O circuit 812. The sensor 816 may be operatively connected to the patient 820. The sensor 816 may include the impedance measuring device 202 and electrodes 206 and 208 discussed in connection to FIG. 2.

The program memory 806 and/or the RAM 810 may store various applications (i.e., machine readable instructions) for execution by the microprocessor 808. For example, an operating system 830 may generally control the operation of the testing apparatus 802 and provide a user interface to the testing apparatus 802 to implement the process 100 described herein. The program memory 806 and/or the RAM 810 may also store a variety of subroutines 832 for accessing specific functions of the testing apparatus 802. By way of example, and without limitation, the subroutines 832 may include, among other things: a subroutine for taking measurements with the sensor 816 and other subroutines, for example, implementing software keyboard functionality, interfacing with other hardware in the testing apparatus 802, etc. For example, the process 100 of FIG. 1 (and instructions elsewhere described herein) may be stored on the program memory 806 for execution by the processor 808. The program memory 806 and/or the RAM 810 may further store data related to the configuration and/or operation of the testing apparatus 802, and/or related to the operation of one or more subroutines 252. For example, the data may be data gathered by the sensor 816, data determined and/or calculated by the processor 808, etc. In addition to the controller 804, the testing apparatus 802 may include other hardware resources. The testing apparatus 802 may also include various types of input/output hardware such as a visual display 826 and input device(s) 828 (e.g., keypad, keyboard, etc.). In an embodiment, the display 826 is touch-sensitive, and may cooperate with a software keyboard routine as one of the software routines 832 to accept user input. It may be advantageous for the testing apparatus to communicate with a broader medical treatment network (not shown) through any of a number of known networking devices and techniques (e.g., through a commuter network such as a hospital or clinic intranet, the Internet, etc.). For example, the testing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system. By way of example, a network interface 834 is coupled to the I/O interface 812 for connecting the testing apparatus 802 to a network 836, through a wired or wireless connection.

In this way, the system 800 may be used to determine the cardiovascular condition of the patient and whether that condition has improved or deteriorated over the period of time, e.g., by measuring changes in venous blood volume over time, and in response to procedures performed by the patient and in response to different treatments provided to the patient. Ventilatory effort of the patient can be determined, e.g., how much effort does it take for a patient to reach a desired volume of inspiration or expiration as measured by impedance and as that correlates to venous blood volume. The cardiovascular condition of a patient can be monitored over time to determine if the condition has improved or deteriorated, e.g., by determining a baseline impedance pattern for a patient and then comparing subsequent impedance measures to that baseline do determine variations from the baseline.

The system 800 may be used to further determine, from the impedance measurements and determined changes in venous blood volume, a central venous pressure or right atrial venous pressure. The system 800 may be further used to determine respiratory rate and respiratory effort, from the change in venous blood volume data. The change in venous blood volume, the respiratory rate, and respiratory effort may be monitored over time to determine if the patient's condition has improved or deteriorated, for example, in response to different treatment cycles and different treatment conditions. In some examples, the system 800 may detect patterns in the changes in volume of blood over a period of time and detect outlines in changes in volume of blood over that time, as indicators of various conditions. In any of these cases, the memory 806 may store the appropriate instructions that are executed by the processor 808 to automatically affect such monitoring and determinations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed:

1. A method for evaluating cardiovascular condition of a patient, the method comprising:
   (a) recording a first impedance of a limb or extremity or neck of the patient at a first time in response to receiving a first impedance reading from a plurality of sensors on a limb or extremity or neck;
   (b) after the occurrence of an event modulating blood return to the heart via the venous system of the patient, recording a second impedance of the limb or extremity or neck at a second time in response to receiving a second impedance reading from a plurality of sensors on a limb or extremity or neck, wherein the first impedance and the second impedance each correspond to a volume of blood flowing within the limb or extremity or neck;
   (c) determining a change in venous blood volume between the first time and the second time by comparing the first impedance and the second impedance to determine a change in volume of blood; and
   (d) determining, based on the change in venous blood volume between the first time and the second time, one or more of:
      (1) how the patient will hemodynamically respond to one or more of an addition of cardiovascular fluid or removal of cardiovascular fluid,
      (2) how the patient will hemodynamically respond to one or more cardiovascular drugs which promote changes in cardiac output, changes in cardiovascular preload, and changes in cardiovascular afterload, or
      (3) how the patient will hemodynamically respond to changes in mechanical or noninvasive ventilation.

2. The method of claim 1, wherein (a)-(c) are performed repeatedly over a period of time, the method further comprising:
   (e) determining whether the cardiovascular condition of the patient has improved or deteriorated over the period of time.

3. The method of claim 2, wherein determining whether the cardiovascular condition of the patient has improved or deteriorated over the period of time includes monitoring the ventilatory effort of the patient and ventilatory dynamics of the patient.

4. The method of claim 2, wherein determining whether the cardiovascular condition of the patient has improved or deteriorated over the period of time includes:
   (1) using a first portion of the recorded impedances to determine a baseline impedance pattern for the patient, and
   (2) comparing a second portion of the recorded impedances to the baseline impedance pattern to detect deviations from the baseline impedance pattern.

5. The method of claim 1, further comprising recording the first impedance and the second impedance using electrodes placed on one of a limb or extremity or neck, where the electrodes includes multiple electrodes to inject electrical current and multiple electrodes to measure impedance.

6. The method of claim 1, wherein the event modulating blood return to the heart includes one or more of spontaneous inspiration, positive pressure mechanical ventilation, raising a limb or extremity or neck of the patient, applying negative or positive pressure to the abdomen or chest, inspiration against a negative impedance valve, or discrete maneuvers performed with mechanical ventilation.

7. The method of claim 6, wherein the discrete maneuvers performed with mechanical ventilation comprise adjusting positive pressure ventilation, negative pressure ventilation, maintaining inspiratory or expiratory pause, or a combination thereof.

8. The method of claim 1, wherein (a) and (b) are performed outside a medical facility.

9. The method of claim 1, wherein the patient is undergoing treatment for one or more of cardiac arrest, edema, burns, trauma, heart failure, sepsis, dehydration, renal failure, or dialysis.

10. A testing apparatus for evaluating cardiovascular condition of a patient, the testing apparatus comprising:
    one or more electrodes;
    one or more processors;
    a computer-readable memory storing non-transient instructions that when executed by the one or more processors cause the testing apparatus to:

(a) use the one or more electrodes to record a first impedance of a limb or extremity or neck of the patient at a first time in response to receiving a first impedance reading from a plurality of sensors on a limb or extremity or neck;

(b) after the occurrence of an event modulating blood return to the heart via the venous system of the patient, use the one or more electrodes to record a second impedance of the limb or extremity or neck at a second time in response to receiving a second impedance reading from a plurality of sensors on a limb or extremity or neck, wherein the first impedance and the second impedance each correspond to a volume of blood flowing within the limb or extremity or neck;

(c) determine a change in venous blood volume between the first time and the second time by comparing the first impedance and the second impedance to determine a change in volume of blood; and (d) determine, based on the change in venous blood volume between the first time and the second time, one or more of:

(1) how the patient will hemodynamically respond to one or more of an addition of cardiovascular fluid or removal of cardiovascular fluid, (2) how the patient will hemodynamically respond to one or more cardiovascular drugs which promote changes in cardiac output, changes in cardiovascular preload, and changes in cardiovascular afterload, or (3) how the patient will respond hemodynamically to changes in mechanical or noninvasive ventilation.

11. The testing apparatus of claim 10, wherein the non-transient instructions include instructions that when executed by the one or more processors cause the testing apparatus to determine whether the cardiovascular condition of the patient has improved or deteriorated over the period of time.

12. The testing apparatus of method of claim 11, wherein the instructions to determine whether the cardiovascular condition of the patient has improved or deteriorated over the period of time includes instructions to monitor a respiratory rate of the patient and a respiratory effort of the patient.

13. The method of claim 12, wherein the instructions to determine whether the cardiovascular condition of the patient has improved or deteriorated over the period of time includes instructions to:

(1) use a first portion of the recorded impedances to determine a baseline impedance pattern for the patient, and (2) compare a second portion of the recorded impedances to the baseline impedance pattern to detect deviations from the baseline impedance pattern.

14. The testing apparatus of claim 10, wherein the one or more electrodes include two electrodes to inject electrical current and two electrodes to measure impedance.

15. The testing apparatus of claim 10, wherein the event modulating blood to return to the heart includes one or more of spontaneous inspiration, positive pressure mechanical ventilation, negative pressure ventilation, or raising a limb or extremity or neck of the patient.

16. The testing apparatus of claim 10, further comprising a photoplethysmograph, a galvanic skin response monitor, a near infrared spectroscopy device, a laser Doppler device with or without speckle tracking, or an ultrasound device with or without speckle tracking.

17. The testing apparatus of claim 10, further comprising impedance cardiography measurement, pulse pressure variation measurement, or stroke volume variation measurement.

18. A closed-loop cardiovascular condition evaluation system comprising:

the testing apparatus of claim 10; and a processor and a memory, the memory storing instructions that when executed by the processor, cause the processor to evaluate a cardiovascular condition of a subject in response to determining the change in the venous blood volume between the first time and the second time determined by comparing the first impedance and the second impedance, for different treatment cycles.

19. The closed-loop system of claim 18, wherein the different treatment cycles comprising, determining the change in venous blood volume under a first treatment condition and under a second treatment condition.

20. The closed-loop system of claim 19, wherein the first treatment condition is a pre-cardiovascular treatment condition and the second treatment condition is after a cardiovascular treatment has been applied.

21. The closed-loop system of claim 18, wherein the memory stores instructions that when executed by the processor, cause the processor to adjust a cardiovascular treatment in response to the determination in the change of venous blood volume.

22. A method for evaluating cardiovascular condition of a patient, the method comprising:

(a) recording a first impedance of a limb or extremity or neck of the patient at a first time in response to receiving a first impedance reading from a plurality of sensors on a limb or extremity or neck;

(b) after the occurrence of an event modulating blood return to the heart via the venous system of the patient, recording a second impedance of the limb or extremity or neck at a second time in response to receiving a second impedance reading from a plurality of sensors on a limb or extremity or neck, wherein the first impedance and the second impedance each correspond to a volume of blood flowing within the limb or extremity or neck;

(c) determining a change in venous blood volume between the first time and the second time by comparing the first impedance and the second impedance to determine a change in volume of blood; and (d) determining, based on the change in venous blood volume between the first time and the second time, one or more of changes in vena cava diameter, central venous pressure, right atrial venous pressure from the change in venous blood volume, or respiratory rate and effort from the change in venous blood volume.

23. The method of claim 22, wherein (a)-(c) are performed repeatedly over a period of time, the method further comprising:

(e) determining whether the cardiovascular condition of the patient has improved or deteriorated over the period of time.

24. The method of claim 23, wherein determining whether the cardiovascular condition of the patient has improved or deteriorated over the period of time comprises:

(1) monitoring the ventilatory effort of the patient and ventilatory dynamics of the patient; and/or (2) using a first portion of the recorded impedances to determine a baseline impedance pattern for the patient and comparing a second portion of the recorded impedances to the baseline impedance pattern to detect deviations from the baseline impedance pattern.

25. The method of claim 22, wherein the event modulating blood return to the heart includes one or more of spontaneous inspiration, positive pressure mechanical ventilation, raising a limb or extremity or neck of the patient, applying negative or positive pressure to the abdomen or chest, inspiration against a negative impedance valve, or discrete maneuvers performed with mechanical ventilation.

26. The method of claim 25, wherein the discrete maneuvers performed with mechanical ventilation comprise adjusting positive pressure ventilation, negative pressure ventilation, maintaining inspiratory or expiratory pause, or a combination thereof.

27. The method of claim 22, wherein (a) and (b) are performed outside a medical facility.

28. The method of claim 22, further comprising recording the first impedance and the second impedance using electrodes placed on one of a limb or extremity or neck, where the electrodes includes multiple electrodes to inject electrical current and multiple electrodes to measure impedance.

\* \* \* \* \*

UNITED STATES PATENT AND TRADEMARK OFFICE
CERTIFICATE OF CORRECTION

| | |
|---|---|
| PATENT NO. | : 10,314,532 B2 |
| APPLICATION NO. | : 14/445926 |
| DATED | : June 11, 2019 |
| INVENTOR(S) | : Kevin Ward et al. |

Page 1 of 1

It is certified that error appears in the above-identified patent and that said Letters Patent is hereby corrected as shown below:

In the Claims

Column 17, Line 39, "of method of" should be -- of --.

Column 17, Line 45, "The method of claim 12," should be -- The testing apparatus of claim 12, --.

Column 17, Line 64, "photoplethysmograph," should be -- photoplethysmography, --.

Signed and Sealed this
Seventh Day of April, 2020

Andrei Iancu
*Director of the United States Patent and Trademark Office*